(12) United States Patent
Ng et al.

(10) Patent No.: US 12,046,368 B2
(45) Date of Patent: Jul. 23, 2024

(54) METHODS FOR TREATMENT OF INFLAMMATORY BOWEL DISEASE

(71) Applicant: Iterative Scopes, Inc., Cambridge, MA (US)

(72) Inventors: Jonathan Ng, Cambridge, MA (US); Jean-Pierre Schott, Weston, MA (US); Daniel Wang, Cambridge, MA (US)

(73) Assignee: Iterative Scopes, Inc., Cambridge, MA (US)

( * ) Notice: Subject to any disclaimer, the term of this patent is extended or adjusted under 35 U.S.C. 154(b) by 339 days.

(21) Appl. No.: 17/383,205

(22) Filed: Jul. 22, 2021

(65) Prior Publication Data
US 2022/0028550 A1 Jan. 27, 2022

Related U.S. Application Data

(60) Provisional application No. 63/055,125, filed on Jul. 22, 2020.

(51) Int. Cl.
*G16H 50/20* (2018.01)
*A61B 1/31* (2006.01)
(Continued)

(52) U.S. Cl.
CPC .............. *G16H 50/20* (2018.01); *A61B 1/31* (2013.01); *A61B 5/7267* (2013.01);
(Continued)

(58) Field of Classification Search
CPC ........ G16H 50/20; G16H 10/60; G16H 30/20; G16H 30/40; G16H 50/30; G16H 50/50; G16H 50/70; G16H 70/60; G16H 10/20; G16H 10/40; A61B 1/31; A61B 5/7267; A61B 5/7275; A61B 1/00009; A61B 1/000094; A61B 1/000096; A61B 5/4255; A61B 5/4848; A61B 1/2736; G06F 18/21; G06F 18/24; G06N 3/08; G06N 3/044;
(Continued)

(56) References Cited

U.S. PATENT DOCUMENTS 7,236,623 B2 6/2007 Chapouland et al.
8,768,024 B1 7/2014 Zingman et al.
(Continued)

OTHER PUBLICATIONS

Stidham et al., jamanetwork.com [online], "Performance of a Deep Learning Model vs Human Reviewers in Grading Endoscopic Disease Severity of Patients With Ulcerative Colitis, " May 17, 2019, retrieved on Sep. 2, 2021, retrieved from URL<https://jamanetwork.com/journals/jamanetworkopen/fullarticle/2733432>, 10 pages.

(Continued)

*Primary Examiner* — Dhaval V Patel
(74) *Attorney, Agent, or Firm* — Fish & Richardson P.C.

(57) ABSTRACT

This specification describes systems and methods for obtaining various patient related data for inflammatory bowel disease (IBD). The methods and systems are configured for using machine learning to determine measurements of various characteristics and provide analysis related to IBD. The methods and systems may also obtain and incorporate electronic health data as well as other relevant data of patients along with endoscopic data to use for prediction IDB progression and recommending treatment.

20 Claims, 7 Drawing Sheets

(51) Int. Cl.
| | |
|---|---|
| *A61B 5/00* | (2006.01) |
| *G06F 18/21* | (2023.01) |
| *G06F 18/24* | (2023.01) |
| *G06N 3/08* | (2023.01) |
| *G06T 7/00* | (2017.01) |
| *G16B 20/00* | (2019.01) |
| *G16B 30/00* | (2019.01) |
| *G16B 40/20* | (2019.01) |
| *G16H 10/60* | (2018.01) |
| *G16H 30/20* | (2018.01) |
| *G16H 30/40* | (2018.01) |
| *G16H 50/30* | (2018.01) |
| *G16H 50/50* | (2018.01) |
| *G16H 50/70* | (2018.01) |
| *G16H 70/60* | (2018.01) |
| *G16H 10/20* | (2018.01) |
| *G16H 10/40* | (2018.01) |

(52) U.S. Cl.
CPC ............ *A61B 5/7275* (2013.01); *G06F 18/21* (2023.01); *G06F 18/24* (2023.01); *G06N 3/08* (2013.01); *G06T 7/0012* (2013.01); *G16B 20/00* (2019.02); *G16B 30/00* (2019.02); *G16B 40/20* (2019.02); *G16H 10/60* (2018.01); *G16H 30/20* (2018.01); *G16H 30/40* (2018.01); *G16H 50/30* (2018.01); *G16H 50/50* (2018.01); *G16H 50/70* (2018.01); *G16H 70/60* (2018.01); *G06T 2207/10068* (2013.01); *G06T 2207/20081* (2013.01); *G06T 2207/30092* (2013.01); *G06V 2201/03* (2022.01); *G16H 10/20* (2018.01); *G16H 10/40* (2018.01)

(58) Field of Classification Search
CPC ........ G06N 3/047; G06N 3/088; G06N 20/10; G06N 3/045; G06T 7/0012; G06T 2207/10068; G06T 2207/20081; G06T 2207/30092; G06T 2207/20084; G16B 20/00; G16B 30/00; G16B 40/20; G06V 2201/03; G06V 2201/031; G06V 10/82
See application file for complete search history.

(56) References Cited

U.S. PATENT DOCUMENTS

| | | | |
|---|---|---|---|
| 9,324,145 B1 * | 4/2016 | Cherevatsky | A61B 1/000094 |
| 11,353,456 B2 | 6/2022 | Oved et al. | |
| 11,574,401 B2 | 2/2023 | Aoyama | |
| 2007/0255095 A1 | 11/2007 | Gilreath et al. | |
| 2008/0085524 A1 | 4/2008 | Lois | |
| 2008/0147087 A1 | 6/2008 | Horn et al. | |
| 2008/0242931 A1 | 10/2008 | Nishino | |
| 2009/0196476 A1 | 8/2009 | Inoue | |
| 2010/0046816 A1 | 2/2010 | Igual-Munoz et al. | |
| 2011/0164126 A1 | 7/2011 | Ambor et al. | |
| 2012/0095331 A1 * | 4/2012 | Ohashi | G06T 7/0014 |
| | | | 600/425 |
| 2013/0070986 A1 * | 3/2013 | Peleg | G06F 18/41 |
| | | | 382/128 |
| 2020/0342958 A1 | 10/2020 | McGovern et al. | |
| 2021/0174958 A1 | 6/2021 | Drake et al. | |
| 2022/0020496 A1 | 1/2022 | Saito et al. | |
| 2022/0028059 A1 | 1/2022 | Ng et al. | |
| 2022/0028547 A1 | 1/2022 | Ng et al. | |
| 2022/0296081 A1 | 9/2022 | Nygaard Espeland et al. | |
| 2023/0036392 A1 | 2/2023 | Kim | |
| 2023/0148834 A1 * | 5/2023 | Baras | G06V 10/764 |
| | | | 382/128 |
| 2023/0154580 A1 | 5/2023 | Wang et al. | |

OTHER PUBLICATIONS

Takenaka et al., "Development and Validation of a Deep Neural Network for Accurate Evaluation of Endoscopic Images From Patients with Ulcerative Colitis," Gastroenterology, Jun. 2020, 158(8):2150-2157.

Vashist et al., "Endoscopic scoring indices for evaluation of disease activity in ulcerative colitis, "John Wiley & Sons, 2018, pp. 1-42.

* cited by examiner

METHODS FOR TREATMENT OF INFLAMMATORY BOWEL DISEASE

CLAIM OF PRIORITY

This application claims priority under 35 U.S.C. § 119(e) to U.S. patent application Ser. No. 63/055,125, filed on Jul. 22, 2020, the entire contents of which are hereby incorporated by reference.

TECHNICAL FIELD

This disclosure generally relates to systems and methods for quantifying and treating diseases such as inflammatory bowel disease, predicting disease progression and treatment outcomes and updating treatment based on the predictions.

BACKGROUND

Inflammatory Bowel Disease (IBD) is a disease which results from a dysregulated and excessive autoimmunity to the intestinal microbiome. IBD is chronic, idiopathic and has a high burden of disease. Patients are susceptible to various anatomical complications during the natural course of disease, as well as opportunistic infections of the gut, which may result in relapses. There are two distinct categories of IBD with differentiable clinical presentation; ulcerative colitis (UC) and Crohn's Disease (CD). Currently, IBD affects 1.4 million Americans and occurs at a prevalence rate of 396 per 100,000 individuals worldwide. IBD tends to appear in patients aged in their 20s to 40s with a demographic peak at 20-30 years for CD and 30-40 years for UC. Up to 15% of patients present with IBD at old age (>65 years).

Endoscopy refers to a nonsurgical procedure used to examine a person's digestive tract. Typically, an endoscope, which is a flexible tube that includes a light and camera, is placed within a patient's digestive tract so that a doctor can view images (e.g., still images and/or video) of the patient's digestive tract. For example, during an upper endoscopy, an endoscope is passed through the mouth and throat into the esophagus of a patient, allowing a doctor to view the esophagus, stomach, and upper part of the small intestine. Similarly, an endoscope can be passed into the large intestine of a patient through the rectum to examine this area of the intestine (e.g., a colonoscopy). Endoscopic procedures allow physicians to evaluate several medical conditions, such as causes of stomach pain, appearances of ulcers, bleeding in the digestive tract, and detection of potential malignancies (e.g., polyps). Endoscopic procedures are a key endpoint for healthcare providers to measure IBD outcome and activity. The FDA also increasingly views endoscopic endpoints (as opposed to patient reported symptoms) as a key measure of drug efficacy and performance for IBD related clinical trials.

The variety of agents used in the treatment of IBD has similarly increased alongside the occurrence of IBD. Besides other medication classes such as 5-ASAs, immunomodulators and corticosteroids, medical service providers increasing use biologics in the treatment of moderate to severe IBD. The use of biologics has become more common and has shown to provide benefits to the treatment of moderate to severe IBD by inducing and maintaining clinical remission, such as reductions in surgeries and hospitalizations. Biologics have improved mucosal healing in patients, improving quality of life.

However, biologics are expensive medications. A study of over 400,000 patients in the U.S. highlights that the costs of an average patient (e.g., in 2015) receiving biologic therapy is nearly eight times costlier and approximately thirty-six times costlier than an average patient receiving 5-ASAs and immunomodulators, respectively. Despite the high prices of biologics, many patients either do not respond or experience a loss response over time towards biologics. It is estimated that between 10 to 40% of patients do not respond to the initial treatment and 23 to 46% of patients lose response over time depending on disease type and trial design. To tackle loss of response, physicians usually either change the drug exposure by modifying the dosage or dosing interval or switch to another drug. Because patients may not respond to the first biologic therapy prescribed, this further raises the cost of care, thus creating a need to develop more personalized and clinically effective ways of prescribing and treating IBD.

SUMMARY

This specification describes systems and methods for predicting disease progression from medical images for inflammatory bowel disease (IBD) and treating the disease (or updating a treatment of the disease) based on the predicted outcomes. The data processing system is configured to combine image classification with analysis of other data, including omics data, registries data, and electronic medical records (EMR) data, as well as time markers to provide patient outcome predictions, therapeutic treatment recommendations, and dosage suggestions. The data processing system is configured to extract data from endoscopy procedures, standardize the data in a data repository, and provide predictions of disease severity and disease progression based on an analysis of the data collected. The recommendations and predictions that are output from this system provide a more data driven approach to IBD treatment and therapeutic assignment, ultimately leading to better patient outcomes and lowered treatment costs.

More specifically, the data processing system is configured to obtain endoscopy data from an endoscopy procedure. The endoscopy data includes medical image data, including video data. The data processing system is configured to perform one or more image processing operations to extract relevant data from the video data and label the video data. The data processing system includes a machine learning module. The machine learning module is configured to receive the labeled video data and perform an analysis of the video data according to one or more approaches. The machine learning module is configured to determine values of various characteristics and features related to IBD that can be used for scoring disease severity and predicting disease progression and activity. The data processing system is configured to obtain and incorporate electronic health data, as well as other relevant patient data (can be both medical and non-medical (i.e. demographic) of patients in combination with the endoscopic video data for generating a prediction of disease progression. The data processing system is configured to recommend treatment to mitigate disease progression or enable a medical service provider to update treatment to mitigate disease progression based on the prediction.

This the systems and methods described herein are configured include methods for scoring images for IBD, described in U.S. patent application Ser. No. 17/164,418 filed in Feb. 1, 2021, the entire contents of which are hereby incorporated by reference in entirety.

The systems and methods described in this specification provide one or more of the following advantages.

Compared to the current standard of manual review, the data processing system is able to provide a prediction of disease progression while taking many different data modalities into account. For example, the data processing system is configured to combine image classification with analysis of other data, including omics data, registries data, and electronic medical records (EMR) data. The predictions generated by the data processing system are more accurate and more consistent than predictions made based on individual doctor knowledge and experiences. The data processing system is more flexible because it includes model interpretability. For example, the data processing system is configured to combine analysis of different kinds of symptoms and colon conditions that are exhibited and note locations within an image frame. For example, the data processing system can identify instances of obliterated vascular patterns in the middle of the frame and one or more instances of bleeding on an edge of the frame.

To support disease progression predictions, the data processing system is configured to generate scoring data that reflect detection of a combination of symptoms, rather than only one of the symptoms. The data processing system is configured to overcome limitations of relying only on image classification to generate predictions of IBD progression. For example, the data processing system overcomes these limitations because objects may not occupy most of the field of view for endoscopy images. In such cases, location specific labels (like segmentations or bounding boxes) are much more informative than image-level labels, even if the amount of location-specific data provided is less than for corresponding label data. Additionally, the data processing system is configured to generate scoring and provide prediction based on data included in Electronic Medical Records (EMR) or Electronic Health Records (EHR), molecular data, omics data, patient reported data and other patient data (e.g., wearables data, data from patient devices, and such similar data where relevant).

Additionally, the data processing system reduces variability in analysis (e.g., relative to manual analysis) by providing computer generated automated scoring, which can result in more consistent and accurate predictions of disease progression and improved treatments of the disease. Currently, a large variability exists between how humans interpret video data. Central readers can be qualified for analyzing patient data when achieving intrarater agreement of only 60%. Currently the assumption is that intrarater variability is somewhere between 10-35%. Relatively high variability results in issues with patient outcomes. For example, because trials are powered to primary end points, the greater the variability, the greater the number of patients that need to be recruited into the trial. This adds tremendous amounts of cost to pharmaceutical companies, not to mention, the bottleneck of not having biologic naïve patients on whom to test these new drugs. Furthermore, scoring is important to track and monitor disease progression in patients. More accurate and precise scoring can generally enable more precise patient monitoring and quicker and more effective treatment adjustments, which generally leads to better patient outcomes. Consistent scoring can also reduce the time and cost to develop new biologic treatments for IBD because reducing scoring variability will reduce the number of patients needed for pharma trials. Furthermore, the current standard of prescribing therapeutic treatments and determining drug dosage results in up to 40% of patients that do not respond to the initial treatment up to 46% of additional patients whose disease fails to response to the drug treatment over time. By using a more data from a wider variety of sources than a doctor may normally look at, and by combining these data sources and analyzing them using proprietary machine learning techniques, better predictions of disease progression, recommendations for drug therapy assignment and more precise dosage prescription could result in better patient outcomes and less time and money wasted on ineffective treatments.

To overcome these issues, the data processing system is configured to provide a more objective, consistent score for endoscopic images, relative to existing scores of such data, by incorporating machine learning and computer vision techniques that reduce intrarater and interrater variability. The data processing system can provide a composite score which captures IBD disease progression (e.g., disease activity) more accurately than existing prediction systems. For example, the data processing system is configured to annotate features of colonoscopy video data and use these features for score generation. The data processing system is configured to generate scores that can be combined with many different types of data. Generally, the data are measured from a same patient for at least two distinct time points or time periods. A machine learning model can process the data from each time period in the context of the processed data of the one or more other time periods. Thus, the machine learning model outcomes are linked to one another for the timeline. The data processing system is configured to predict how the disease will progress over time in the patient, and recommend a treatment based on the prediction.

The one or more advantages are enabled by one or more embodiments. A method for predicting inflammatory bowel disease (IBD) activity in a patient and prescribing treatment for IBD, includes: obtaining image data including endoscopic images of a gastrointestinal tract (GI) of a patient for a first time period and a second time period;
   determining one or more features to extract from the image data, the features each representing a physical parameter of the GI tract for each of the first time period and the second time period; extracting the one or more features from the image data to form a first feature vector for the first time period and a second feature vector for the second time period; selecting a machine learning model based on the one or more features included in the first feature vector and the second feature vector; processing the first feature vector and the second feature vector using the machine learning model, the machine learning model being trained with labeled image data representing instances of symptoms of IBD being in the GI tract, the labeled image data associating scores representing a progression of IBD based on the respective instances of the symptoms in the first and second vectors; determining, based on the processing, a prediction of disease progression of IBD in the patient; and storing, in a data store, the prediction in association with the image data.

In some implementations, determining the prediction comprises: determining one or more frame level annotations corresponding to individual frames of a video of the image data; determining one or more case level annotations for the video of the image data; and determining, based on the one or more frame level annotations and the one or more case level annotations, the prediction of disease progression of IBD in the patient.

In some implementations, the one or more features comprise values representing at least one of: a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal; and wherein the prediction of disease progression of IBD in the patient is based on the values of the one or more features.

In some implementations, the method includes receiving electronic medical records (EMR) data for the patient, the EMR data including medical information about the patient, wherein the machine learning model is trained with labeled EMR data associating values of medical information of patients with respective severity of IBD in the patients; extracting one or more values from the EMR data to form an EMR feature vector; processing, by the machine learning model or by a second machine learning model in addition to the machine learning model, the EMR feature vector; and generating an updated prediction of disease progression of IBD in the patient indicated by the EMR data.

In some implementations, the one or more features of the EMR feature vector comprise values representing at least one of: an age of the patient, a sex of the patient, a reproductive history of the patient, a smoking status of the patient, a race or ethnicity of the patient, a presence or absence of an anal fissure in the patient, a fistula or abscess in the patient, and the presence or absence of one or more complications such as uveitis, pyoderma gangernosum, erythema nodosum, and/or arthralgia in the patient, serological profiling results of the patient, a history of medications prescribed to the patient, a history of surgery for the patient, a degree of induration for the patient, a presence or size of an abdominal mass in the patient, a history of flaring in the patient, a hospitalization history for the patient, and a history of thrombosis for the patient.

In some implementations, the method includes receiving registry data for the patient, the registry data including patient data across patient populations, wherein the machine learning model is trained with labeled registry data associating values of for patient populations with respective severity of IBD in particular patients of the patient populations; extracting one or more values from the registry data to form a registry feature vector; processing, by the machine learning model or by a second machine learning model in addition to the machine learning model, the registry feature vector; and generating an updated prediction of disease progression of IBD in the patient indicated by the registry data.

In some implementations, the one or more features of the registry feature vector comprise values representing at least one of: results and other data from studies, experiments, and clinical trials that test treatment regimens that are associated with the patient including one or more of drug therapy, physical therapy, or surgery, specific diagnoses associated with the patient, procedures, and application of drugs associated with the patient.

In some implementations, the process includes receiving omics data for the patient, the omics data including genetic or molecular profiles of patient populations, wherein the machine learning model is trained with labeled omics data associating values of genetic or molecular profiles with respective severity of IBD in the patients of the patient populations; extracting one or more values from the omics data to form an omics feature vector; processing, by the machine learning model or by a second machine learning model in addition to the machine learning model, the omics feature vector; and generating an updated prediction of disease progression of IBD in the patient indicated by the omics data.

In some implementations, the one or more features of the omics feature vector comprise values representing at least one of: transcriptomics data such as sets of RNA molecules, including mRNA, rRNA, tRNA, and other non-coding RNAs relevant to treatment outcomes; one or more phenotypic traits of the patient; microbiome data for the patient; genome sequencing for the patient; bisulfate sequencing (RRBS) data of the patient; ChIP-sequencing for the patient; HLA-DR genotyping for the patient; a 16s microbiome sequence from stool of the patient; a 16s microbiome sequence from a biopsy of the patient; epithelial cell profiling from biopsy of the patient; a single cell assay from a biopsy of the patient; a single-cell RNA sequence from a biopsy of the patient; fecal calprotectin or lactoferrin of the patient; Haematocrit levels for the patient; serum CRP/C-reactive protein levels in the patient; Pharmacokinetics (PK) data associated with a patient; white blood cell counts (WBC), hemoglobin (HgB), platelets, albumin, creatinine, and/or ESR levels of the patient; a urea analysis of the patient; liver function tests of the patient; ferritin, B12, Folate and/or VitD levels in the patient; SCFA levels in stool of the patient; and basal metabolite panel in the patient.

In some implementations, the machine learning model comprises a convolutional neural network (CNN) or other models, and wherein the each of the instances of symptoms of IBD contributes to an activation value for inputting into a layer of the CNN.

In some implementations, processing the feature vector comprises performing a classification with detection bounding boxes and segmentation pixel-wise masks on the image data.

In some implementations, the method includes generating the machine learning model by: receiving image data including ground truth scores; labeling the image data; performing frame sampling and score assignment to the frames; applying training data to the machine learning model at a frame level and at a case level; optimizing the machine learning model with validation data at the frame level and the case level; applying test data that is not annotated; and performing case level evaluation of the test data.

In some implementations, the method includes applying a second machine learning model that is different from the machine learning model, to patient data representing a treatment outcome for a treatment between the first time period and the second time period; generating, by the second machine learning model based on applying the second machine learning model to the patient data, a second prediction of disease progression of IBD in the patient; and generating, based on the prediction and the second prediction, a recommendation for a treatment for IBD for the patient for a future time period.

The methods described herein can be performed by systems, such as a system for predicting inflammatory bowel disease (IBD) activity in a patient and prescribing treatment for IBD, the system comprising: at least one processor; and at least one memory storing instructions that, when executing by the at least one processor, cause the at least one processor to perform the operations of the method.

The methods described herein can performed by execution of software, such as on one or more non-transitory computer readable media storing instructions predicting inflammatory bowel disease (IBD) activity in a patient and prescribing treatment for IBD, the instructions configured to cause at least one processor executing the instructions to perform the operations previously described.

These and other aspects, features, and implementations can be expressed as methods, apparatus, systems, components, program products, means or steps for performing a function, and in other ways. These and other aspects, features, and implementations will become apparent from the following descriptions, including the claims.

DETAILED DESCRIPTION

Figure 1:
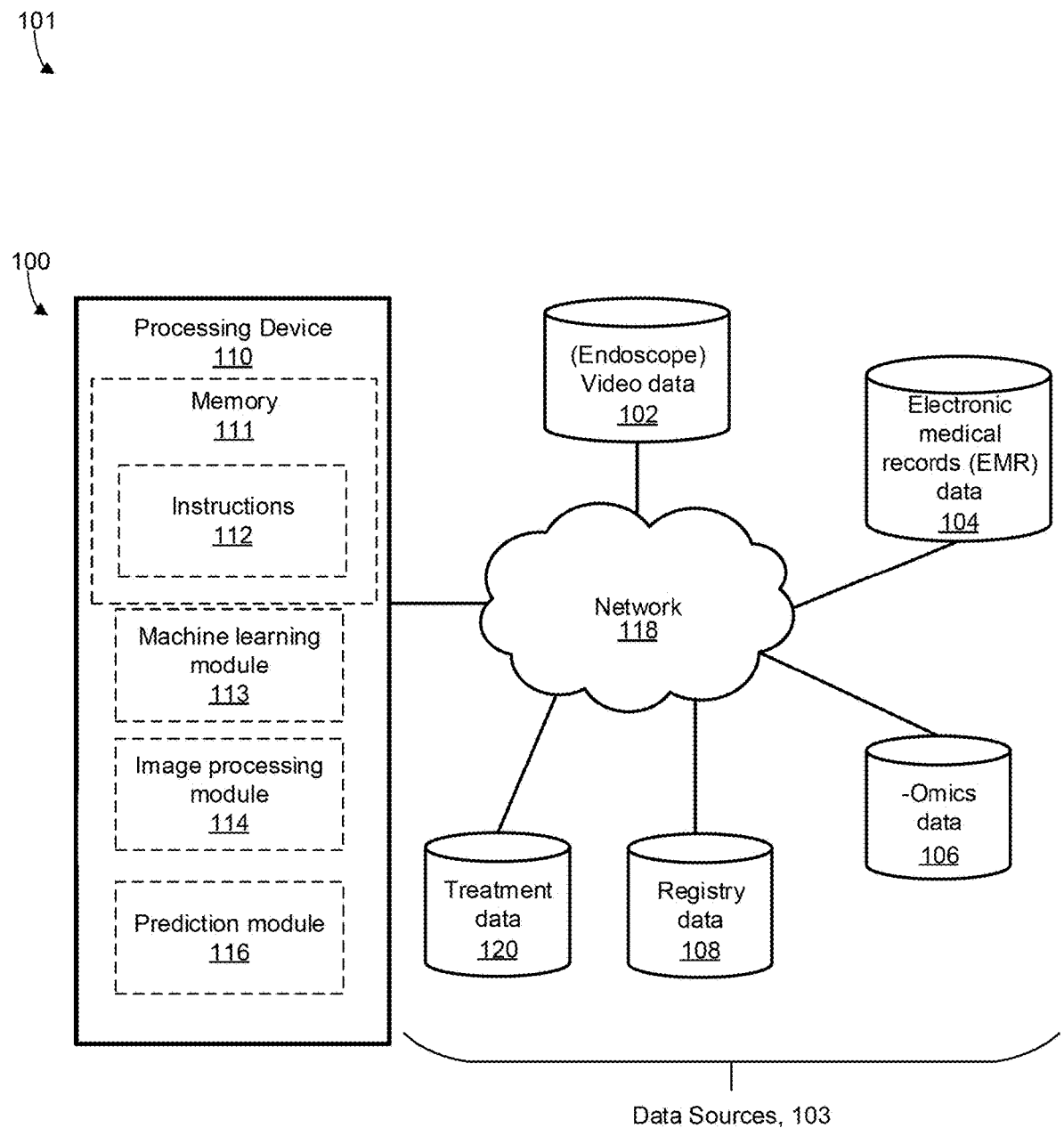
FIG. 1 shows a data processing system for prediction disease progression and recommending one or more treatments for IBD.

FIG. 1 shows an example of a data processing system 100 configured to execute one or more processes for an automated analysis of endoscopic and other health data for inflammatory bowel disease (IBD) classification and treatment. The data processing system includes a processing device 110, a memory 111 (or a computer readable hardware storage device) configured to host instructions 112, a machine learning system 113 configured to execute one or more trained machine learning platforms, an image processing module 114, and a prediction module 116.

The data processing system 100 is configured for using machine learning (e.g. of the machine learning module 113, described below) to determine measurements of various characteristics related to IBD. The data processing system 100 is configured to obtain and incorporate data from various sources for training the machine learning system 113, performing scoring (e.g., by a scoring module) of endoscope video data 102. For example, the data processing system 100 includes electronic health records or electronic medical records (EMR) data 104 of patients in addition to video (endoscope) data 102 to use for scoring. The data processing system 100 also accesses-omics data 106 and registry data 108 for training the machine learning system 113 and performing scoring. In some implementations, functions of one or more of modules 113, 114, and/or 116 can be combined in part or in whole.

The data processing system 100 processes data from one or more of data sources 103. The data sources include video data 102, electronic medical records 104, -omics data 106, registry data 108, and treatment data 120. Each of these data sources 103 is subsequently described in further detail. These data sources 103 can be used individually or in any combination for generating enhanced scores for IBD. For example, video data 102 alone may be sufficient to generate a confident score for a particular patient. In another example, video data 102 can be supplemented with EMR data 104, -omics data 106, etc. to increase confidence in a particular score or in an initial iteration of scoring.

The data processing system 100 is configured to obtain video data 102 from an endoscopic tower or endoscopic processing unit (not shown). The endoscopic tower includes an imaging device that is configured to capture image data or video data 102. In some implementations, the imaging device is an endoscope. An endoscope is an illuminated optical, thin, and tubular instrument (e.g., borescope) used to examine internal organs like the throat or esophagus. The endoscope can be shaped and configured to target specific organs, such as the bladder, kidney, bronchus, colon, and/or pelvis. In some implementations, the endoscope is flexible and includes a camera on one end. The camera can capture image data in the form of still images and/or video. The image or video data 102 can take the form of several data formats, such as RAW, JPEG, PNG, etc. In some implementations, the imaging device includes a digital camera that uses a charge-coupled device (CCD) and/or complementary metal oxide semiconductor (CMOS) to convert photons to electrons for digital processing.

The EMR data 104 includes records associated with individual patients. The EMR data 104 can include self-reported data of the patient. The EMR data 104 can include data obtained from physicians or other medical service providers from interacting with the patient. For example, the EMR data 104 can include a medical history for the patient, such as medical operations the patient has experienced, illnesses the patient has experienced, and physiological data associated with the patient.

The omics data 106 includes genetic or molecular profiles of humans. The omics data 106 includes genomes and the inter-relationships of particular genes. The omics data 106 can be used to provide context to other patient data, such as data acquired from patient registries 108 and/or from EMR data 104.

The registries data 108 includes a clinical data registry, all called a patient registry or disease registry. The registries data 108 includes a database that collects, organizes, and displays healthcare information, generally related to a particular disease and for a patient population. The registries data 108 can be structured such that trends across patient populations are identifiable. For example, the trends can indicate how patients have responded to various IBD treatments. The trends can associate symptoms with scores that have been assigned to those symptoms and how the scores changed in response to particular treatments. The registries data 108 can be combined with the omics data 106 and the EMR data 104 to establish patient trends and track treatment outcomes.

The data processing system 100 is configured to use machine learning techniques to generate a patient score for IBD and to predict disease progression for the patient. The machine learning techniques replicate how physicians interpret endoscope images. For example, the data processing system 100 determines which types of drugs are effective based on the level of activity of IBD seen in the images. The level of activity of IBD is based on a number of various sub-classifications represented in images or video obtained from the endoscope. These sub-classifications can include determining the presence of bleeding, inflammation, polyps, or similar symptoms that may occur from IBD. This process is subsequently described in greater detail with respect to the machine learning module 113, the image processing module 114, and the prediction module 116.

The data processing system 100 is configured to automate various IBD classification scores (i.e. Mayo Score, etc.), as previously indicated. The data processing system 100 ingests data from various sources, such as image or video data 102, EMR data 104, -omics data 106, and registry data 108. While data sources 102, 104, 106, and 108 are shown in FIG. 1, this list is not exhaustive. Patient data from other sources can also be incorporated into analysis for automation of scoring.

The data processing system 100 is configured to receive video or image data 102 from a procedure (e.g., from a colonoscopy). The image or video data 102 generally includes a sequence of frames, each representing a portion of the colon (or other such patient data). A subset of the frames or images of the video or image data 102 can represent symptoms of IBD. The data processing system 100 is configured to identify the frames or images of the data 102 that represent symptoms and score the video including the frames accordingly.

The image processing module 114 is configured to process the image or video data 102 for identifying the presence of symptoms of IBD. In some implementations, the image processing module 114 is a part of the machine learning module 113, wherein the image processing module extracts data from the images or videos, and the machine learning module 113 performs classification of the extracted data. For example, the image processing module 114 may perform thresholding operations or feature extraction based on signals received from the machine learning module 113 (e.g., setting threshold values or identifying features in the images to extract).

The image processing module 114 can process the images or frames of the video data 102 on an individual basis and/or in combination with one another to identify the presence of IBD symptoms (e.g., bleeding, ulcers or sores, narrowing of the intestines, and so forth). For example, the image processing module 114 can process images frame by frame to identify a symptom presence in the frame (e.g., by signature matching a region of the image to a known signature representing a symptom). In some implementations, the image processing module 114 is configured to identify where in the image the symptom is manifested and identify, to other module (such as the machine learning module 113) which frames or sequence of frames are associated with a symptom.

The image processing module 114 generally is configured to draw bounding boxes or otherwise tag or identify images or frames as representing a symptom. However, how the image processing module 114 identifies the symptoms can be changed or updated based on feedback from the machine learning module 113. For example, the image processing module 114 can extract image data based on thresholds set or adjusted by the machine learning module 113. In some implementations, the machine learning module 113 is configured to update, based on training data, image signature data used for classification of the image or video data.

The image processing module 114 can process groups of frames or images of video data 102 together to identify a symptom. For example, if a symptom appears in single frame of the video, the identification of the symptom may be a false positive. The image processing module 114 can be configured to analyze the image in the context of a previous frame (or series of frames) or a subsequent frame (or series of frames). The image processing module 114 is configured to facilitate extraction and/or recognition, from image data, of features that inform generating of the classification score (e.g., by the machine learning module 113). For example, the image processing module 114 can facilitate detection of bleeding, polyp formation, etc. by applying one or more feature extraction processes using image processing. For example, these processes can include object detection, pixel thresholding, application of filters to the images or portions of the images, and so forth.

The machine learning module 113 is configured to classify the data from the data sources 102, 104, 106, and 108 to determine a prediction of IBD progression in the patient. For example, for video data 102, the machine learning module 113 is configured to regress IBD classification scores from single frames or video clips to enable the prediction module 116 to generate a prediction of IBD severity in the patient.

The machine learning module 113 trains convolutional neural networks (CNNs) to classify video frames or video clips. In some implementations, many frames with scores can be quickly obtained by defining intervals in videos with constant scores. The machine learning module 113 disregards outlying frames (e.g., frames including a representation sprayed water) that may not positively contribute to score regression. The machine learning module 113 is configured for transfer learning to generate a score from features trained with different datasets. For example, an IBD classification score can be updated based on features learned for polyp detection (e.g., based on image processing processes previously described).

In some implementations, the machine learning module 113 includes a plurality of machine learning models. Each model of the plurality can be configured to process data from one of the data sources 103 (e.g., video data 102, EMR 104, omics data 106, and registry data 108) of data available to the data processing system 100. In some implementations, a single machine learning model is configured to receive data from two or more of data sources 103 and use those data in combination for generating a classification output. For example, a machine learning module 113 can receive image data 102 showing that inflammation is present in a patient's colon. In addition, the patient may have reported diarrhea symptoms, which can be captured in that patient's EMR data 104. These data together may suggest a stronger IBD classification output. In some implementations, these data are processed by separate models, and the prediction module 116, further described below, combines this data into a prediction of IBD progression in the patient.

In some implementations, the machine learning models are developed from data of different, unrelated diseases, such as IBD and colorectal cancer. Generally, each set of training data is sourced from various clinical datasets, including those from pharmaceutical drug clinical trials, representing specific patients set or modalities. The data processing system 100 is configured to apply transfer learning between patients associated with different locations and different modalities from one another.

In an embodiment, the data processing system 100 performs an automated regression of various IBD classification scores using the machine learning module 113. The machine learning module 113 obtains pre-existing videos and data from data sources 103. The machine learning module 113 annotates these data to derive an updated classification score for the image data 102. The machine learning module 113 receives data 103 from third parties such as hospitals and clinics. The data 103 received can be unstructured data that are transformed for use in the data model (e.g., in one or more machine learning models of the module 113). The data processing system 100 is configured to perform a multi-pronged approach to development of a machine learning model enhancing the generated predictions based on other features extracted from the data 103. The features extracted from this data can evolve as the models are trained. For example, the machine learning module 113 may be configured for segmenting ulcers at scale, identifying particular trends in the registries data 108, identifying symptoms from patient provided data in EMR records 104, and so forth. The machine learning module 113 passes the classification data to a prediction of disease progression as represented by the endoscopic data and the data from data sources 103

In some implementations, the data collected are from a given patient from a particular time point. Disease progression is tracked in a patient by observing patient symptoms for weeks, months or years. Different statuses of the patient are tracked, such as whether the patient is receiving drugs (e.g., yes or no), or what type of drug and what dosage is being received. Outcomes are correlated from one observation (e.g., set of measurement data of the patient a particular time) to another observation (e.g., a second set of measurement data of the same modalities at a second, later time). The disease progression is tracked for a specific symptom. For example, a specific portion of a patient's colon is tracked over time and associated with multiple sets of measurement data over that time.

Based on the analysis by the machine learning module 113, a prediction module 116 of the data processing system 100 is configured to generate a prediction based on the classification data output from the machine learning module 113. As subsequently described, the data processing system 100 receives data from a variety of sources 103, and ensures homogeneity amongst the data before the data is used for training of the machine learning model at module 113. The data processing system 100 is configured to perform data curation, which includes all the processes needed for principled and controlled data creation, maintenance, and management, together with the capacity to add value to data and data normalization that insure that a given data class with many sources such as video data from multiple clinical sites or EHR from various health system have compatible ensemble statistics. For example, video data are resampled to the same size and resolution and contrast and intensity normalized to have similar mean and standard deviation.

The data processing system 100 extracts the data from sources 103 and standardizes the data in a data repository (e.g., data store 201 subsequently described). The data processing system 100 is configured to segment the data based on time markers into three or more distinctive time frames. These time frames could be at weeks 0, 12 and 52, or they could be at other intervals. The data processing system 100 uses a combination of the data from the various time frames (in our example, weeks 0 and 12) to predict outcomes for week 52. In some implementations, the prediction can represent a patient disease progression for that time frame. In some implementations, the prediction can include additional recommendations such as treatment assignment and dosage suggestions. The prediction module 116 generates data that represents a prediction of how the detected symptoms in the patient (e.g., identified from the image data or other data sources) will progress in the future, and therefore recommend a treatment based on that disease progression. For example, if the disease with current treatment is predicted to become more severe in the future based on data presented, the prediction module may indicate as such and generate a recommendation that the dosage of the current drug be modified (increased), the addition of a new drug to assist in treatment or to switch the treatment altogether. However, other recommendations are possible. For example, outcomes where the disease with the current treatment is predicted to become neutral or improve, then smaller adjustment (changes in dosage) or no adjustments may be recommended.

Generally, based on the prediction of disease progression, the data processing system 100 is configured to recommend a drug therapy for the patient in the near or long term. The recommendation can be a change from a prior treatment recommendation. For example, the treatment recommendations include a specified drug regimen for a patient. The data processing system 100 correlates disease progression over time (e.g., week 0 and week 6) for a particular symptom, group of symptoms, or location in the patient. The data processing system 100 determines a rate or projected "slope" of disease progression based on each measurement set, the data processing system 100 is configured to extrapolate outcomes at distant time periods in the future (e.g., 52 weeks). The data processing system 100 can compare this projection to measured outcomes of other cohort patients and estimate whether a particular drug being observed is to be neutral, less effective, or more effective on a given patient. As previously stated, patient demographics are also included in the measurement sets and used to train the machine learning models for each disease.

The prediction module 116 generates a prediction output and associated treatment recommendation that is a combination of automated regression or classification and extracted features to represent a validated prediction. The data processing system 100 performs a multi-week or multi-month correlation of a state of the patient for each given symptom, rather than applying a single data point to the machine learning model. The data processing system 100 is thus configured to generate an increasingly complex prediction of disease progression based on endoscopic image data 102 in the context of both clinical and molecular data. The prediction represents a confidence in a particular clinical outcome if the status quo (e.g., maintaining current treatment level or no treatment) is maintained for future time period. The time period can be days, weeks, or months in the future (or a combination thereof). The prediction is generally paired with a recommendation of a treatment to achieve a more preferable outcome, such as curing symptoms or reducing IBD severity, if applicable. The prediction ensures that treatment regimens that are currently being performed, if predicted to be ineffective, are changed. The prediction ensures that unnecessary treatments, such as application of medication that may be costly or have undesirable side effects, is minimized.

The prediction module 116 generally receives feature classification data from the machine learning module 113. However, the prediction module 116, and machine learning module 113 can be combined or can be separate modules executed by the processing device 110. In some implementations, the prediction module 116 is a portion of the machine learning module 113. In some implementations, the prediction module 116 receives input from the machine learning module 113 and uses the classifications of one or more machine learning models (e.g., for processing data from different sources 102, 104, 106, and 108) in a voting system to generate the score. In some implementations, the prediction module 116 uses a weighted average of classification values output from machine learning models of the machine learning module 113 or receive from another source. For example, the prediction module 116 may receive a strong classification from a polyp identification machine learning model, and receive data from EMR in which the patient reported bleeding. The prediction module 116 may combine these data to generate a prediction that IBD in the patient is present. The prediction module 116 may generate a more accurate prediction of disease progression (e.g., that IBD will become more severe in the short term) than would be generated from the machine learning model output in isolation. In some implementations, the prediction module 116 can receive conflicting classification outputs form machine learning modules or conflicting data from data sources 103. In this case, the prediction module 116 may generate prediction of slow/non-progression, despite a particular machine learning model outputting a classification output representing a strong indication that IBD will increase in severity in the patient. Thus, the inclusion of data from many sources 103 results in a more robust severity score output than a score generated from a particular data source 102, 104, 106, or 108 in isolation. This severity score is then combined with other data sources 103 again to be used to predict disease progression and make treatment recommendations, as described herein.

The prediction from the prediction module 116 is presented to a user of the data processing system 100. The prediction can be presented as a value (e.g., a number), as a string (e.g., text), or in any similar format. In some implementations, the prediction is used to cause a data processing operation to occur based on the value of the prediction. For example, data from all or some or one of the data sources (103) or from the score generated across at least two different time periods is used to generate a prediction that the disease will increase in severity over a period of time (can be variable) above a particular threshold value, the data processing system 100 can be configured to generate an alert, alarm, generate a message, recommend immediate care, or perform some other operation. For example, if the prediction severity exceeds a threshold value, the data processing system 100 can be configured to alert a medical service provider or provide a particular visualization (which could include changing treatment type or dosage levels). If the score is below the threshold, the data processing system 100 can be configured to provide a different visualization. In some implementations, a patient record associated with the patient can be automatically updated to include prediction and treatment recommendation.

The computer-readable hardware storage device 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the memory 111 (e.g., computer-readable hardware storage device) includes code-segment (or other executable logic) having executable instructions.

The computer processors 110 can be communicatively coupled to a video capture device and configured to receive spatially arranged image data (e.g., video data) corresponding with one or more images captured by the imaging device. In some implementations, the computer processors 110 include a general purpose processor. In some implementations, the computer processors 110 include at least one applicable inference processor, accelerated processor which can be utilized in half, single, or double precision (16, 32, or 64 bit floating-point) calculation. The computer processor 110 can also include lots of compute unified device architecture (CUDA) cores, etc., or a combination of thereof. In some implementations, the computer processors 110 include a central processing unit (CPU). In some implementations, the computer processors 110 include at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code means such as the computer-executable instructions 112.

In some implementations, the network 118 enables a cloud-based or web-based system for processing the data. For example, the data processing system 100 can be operated as a web-based service over the network 118. In some implementations, the data sources 103 can be cloud-based and accessible remotely over network 118.

The data processing system can include a display unit (not shown) that is communicatively coupled to the computer processors 110 and configured to show results of the scoring and prediction processes described herein. The display unit can include an electronic display device. In some implementations, the display unit can be configured to act as a touchscreen display device. The display unit is configured to present a user interface. In some implementations, the user interface is a graphical user interface (GUI). The user interface is configured to allow a user of the data processing system 100 to interact with the data processing system 100 through graphical icons and visual indicators. The user interface can use a windows, icons, menus, pointer paradigm (WIMP) to allow a user to interact with the data processing system 100. In some implementations, the user interface 121 cooperates with the 120 to provide a user with a touchscreen GUI. Additionally, or alternatively, the user interface can include one or more input devices such as a mouse and/or keyboard communicatively coupled with the system 100. The user interface can also use a post-WIMP paradigm typically found in touchscreen-based GUIs. In some implementations, the user interface is configured to display images in the form of still photographs and/or videos.

In some implementations, the user interface includes a marker indicating a relative risk for the disease progression (e.g., severe, moderate, mild, none). For example, the data processing system 100 is configured to output a recommendation accompanied by a visual cue representing the disease progression prediction. In some implementations, the data processing system 100 is configured to mark "bad" data that was ineffective for assisting providing the recommendation, such as if the lens of a camera during an endoscopy was obscured. This may indicate to the user that more data are required (e.g., another observation or measurement set) for updating the disease progression prediction.

Figure 2A:
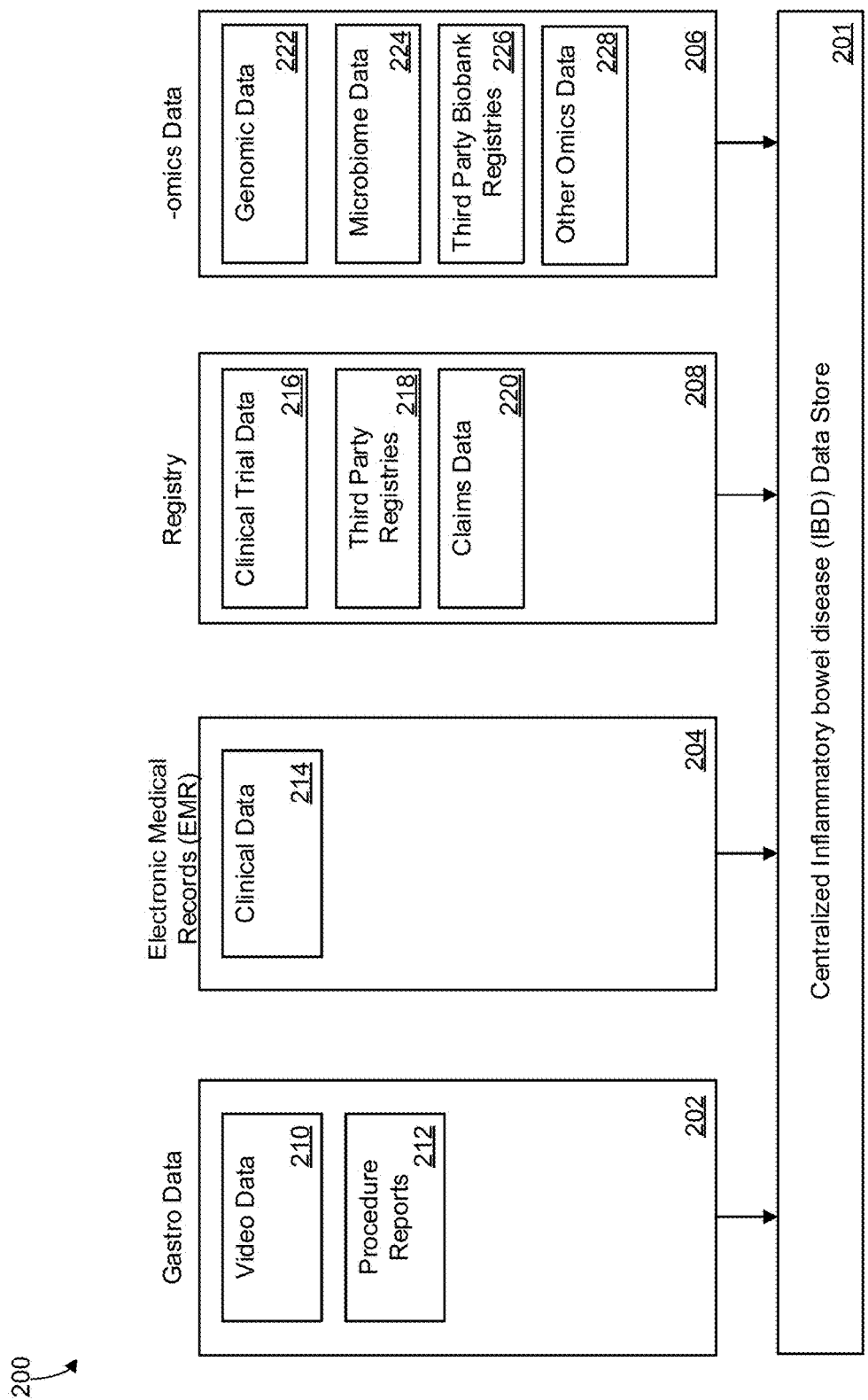
FIG. 2A shows example data sources for training and developing machine learning models for detection of IBD, prediction of disease progression and recommendation of one or more treatments for IBD.

FIG. 2 shows example data sources 200 for training and developing machine learning models for detection of IBD activity. Data sources 200 correspond to data sources 103 of FIG. 1. The data processing system 100 of FIG. 1 can be configured to communicate with a centralized IBD data store 201. The centralized data store 201 is configured to communicate with each of the data sources including the gastro data 202, the EMR data 204 (e.g., similar to EMR data 104), the registry data 208 (e.g., similar to registry data 108), and the -omics data 206 (e.g., similar to -omics data 106 of FIG. 1). Generally, the centralized data store 201 can store data from multiple individual data sources 202, 204, 206, and 208 in a common structured system. For example, the data sources 202, 204, 206, and 208 can be 3rd party data sources or segmented data stores confined to particular data formats, particular data structures, and/or particular data accessible by particular systems. The centralized data store 201 retrieves data from the sources 202, 204, 206, and 208 can combine the data in to facilitate processing by the machine learning module 113, prediction module 116, and so forth for the data processing system 100.

As previously described, the data processing system 100 is configured to store these data or portions thereof in a data store 201 for analysis. Data store 201 represents an interface for accessing the data from various sources 103; the actual data need not be stored in a centralized database. For example, various data of sources 103 that are collected for analysis reside in various systems and generally include a superset of information is useful for analysis an aggregation. The data 202, 204, 206, or 208, or a portion thereof, can be included in a relational database. The data 202, 204, 206, or 208, or a portion thereof, can be part of a specific EMR or HER system and can be ingested and stored in cloud buckets. These data can be searched directly from the files stored using data connectors. Other data such as omics data, such as omics data 206, are too large to be incorporated in traditional databases but derivatives of these data can be generated such as gene variants, gene expression and pathway analysis or aggregates that represent specific subpopulation can be generated and are useful to describe behavior a particular subset of patients.

As previously described, the data processing system 100 is configured to ensure homogeneity amongst the data before the data is used for training of the neural network(s), such as through data curation. In an example, the data processing system 100 curates EHR and EMR data 204 entails adding timestamps across all datasets. Missing variables can be assigned by applying a Bayesian regression and standard statistics for feature selection can be used to determine the continuous baseline variables for significant differences between the one-year endoscopic remission and active groups.

The gastro data 202 generally includes data related to endoscopic procedures. For example, the gastro data 202 can include video data 210 (e.g., similar to the video data 102 previously described). The gastro data 202 can also include other data associated with the endoscopic procedure used to acquire the video data 210. For example, the gastro data 202 can include procedure reports 212 that include data about the patient when the procedure was performed, how the procedure was performed and what the video data represents (e.g., a particular region of the intestines or other portion of the body). The procedure reports 212 can include any data provided by the patient or the medical service provider that is related to the procedure.

The EMR data 204 include medical records for particular patients (similar to EMR data 104 previously described). The EMR data 204 can include data that conform to standard forms. The EMR data 204 can include clinical data for a patient that is provided by a medical service provider in response to a patient visit or telehealth interaction. Generally, the EMR data 204 are on a per-patient basis. This provides a rich history for a particular patient, and the patient's EMR data 204 can be imported to the centralized IBD data store 201 when the patient data is being processed by the data processing system 100.

The gastro data 202 includes features that are used for classifiers for the machine learning models subsequently described. The values of the feature data affect how the scoring is performed by the machine learning model. For example, an endoscopy classifier receives feature data describing the patient as received from endoscopy procedures of the patient. These features can be represented in the video data 102. The values of the features affect how the machine learning model classifies the prediction for disease progression in the patient. The gastro data 202 features can include values that represent, for an endoscopy classifier, one or more of the following. The gastro data 202 features can include values that represent a location of the endoscopy, such as a lower GI endoscopy. The gastro data 202 features can include values that represent a presence of ulcers and/or a number of ulcers. The gastro data 202 features can include values that represent a relative vascularity, such as a percentage decrease of vascularity. The gastro data 202 features can include values that represent presence of erosions, and a number of the erosions. The gastro data 202 features can include values that represent presence or absence of bleeding in the GI tract, and a number of times bleeding was observed (e.g., a number of frames including evidence of bleeding). The gastro data 202 features can include values that represent erythema in GI tract). The gastro data 202 features can include values that represent a friability (e.g., in GI tract). The gastro data 202 features can include values that represent a size of ulcers or erosions. The gastro data 202 features can include values that represent a presence of stenosis (e.g., narrowings) of the GI tract. The gastro data 202 features can include values that are associated with an upper GI endoscopy (e.g., that specified as located in the upper GI endoscope data). The gastro data 202 features can include values that represent a total ulcerated surface (e.g., presence or absence of this surface, and a percentage of the tract including such a surface). The gastro data 202 features can include values that represent a surface affected by disease (e.g., as a percentage of the total surface). The gastro data 202 features can include values that represent a disease location in GI tract. The gastro data 202 features can include values that represent a number of lesions observed (e.g., at the case level). The gastro data 202 features can include values that represent a presence of cobblestoning in the tract. The gastro data 202 features can include values that represent a presence of deep ulcers. The gastro data 202 features can include values that represent a type of Crohn's disease observed (e.g., non-stricturing, non-penetrating, stricturing, penetrating, stricturing and penetrating, or perianal). The gastro data 202 features can include values that represent a presence of dysplasia in the patient. The gastro data 202 features can include values that represent whether activity at a biopsy site is proximal or distal.

The EMR data 204 includes data representing features that are used for classifiers for the machine learning models subsequently described. For example, a concomitant medications classifier contributes value to the prediction of disease progression based on whether these medications are being used by the patient. The data can include whether the patient is using diphenoxylate or opiates as anti-diarrheal medication. The values of the feature data affect how the scoring is performed by the machine learning model. In another example, a demographic classifier receives feature data including demographics data about the patient, which can affect how scoring is performed. For example, the demographics features can include age, sex, reproductive history, smoking status, and race or ethnicity. In another example, a physical examination classifier receives feature data including patient data obtained from physically examining the patient by a physician. For example, the features for this classifier can include data from a patient medical history which may indicate ileocolonic resection. The feature data can include data indicative of one or more of the presence or absence of an anal fissure, a fistula or abscess, and the presence or absence of one or more complications such as uveitis, pyoderma gangernosum, erythema nodosum, and/or arthralgia. The feature data can include data from physicians' global assessment of the patient (e.g., indicating the presence or absence of a condition). The EMR data 204 features can include values from pathology laboratory results, such as representing serological profiling results for a time period. The feature data include data values representing a history of medications prescribed to the patient, including current medications and biologics. The EMR data 204 features can include values that represent whether the patient has used biologics. The EMR data 204 features can include values that represent disease activity (e.g., whether a disease is active or inactive). The EMR data 204 features can include values that represent an IBD type, such as whether the type includes UC or CD. The EMR data 204 features can include values that represent a disease duration (e.g., in years). The EMR data 204 features can include values that represent a history of surgery for the patient (e.g., whether it has occurred, what surgery has occurred, and when surgery has occurred). The EMR data 204 features can include values that represent whether steroid-free remission has occurred. The EMR data 204 features can include values that represent fistula drainage (e.g., an extent or occurrence). The EMR data 204 features can include values that represent whether the patient has experienced pain or activity restriction (e.g., frequency and severity values associated with either or both). The EMR data 204 features can include values that represent a degree of induration for the patient. The EMR data 204 features can include values that represent a presence or size of an abdominal mass in the patient. The EMR data 204 features can include values that represent whether sexual activity has been restricted. The EMR data 204 features can include values that represent a history of flaring (e.g., during a study associated with the patient). The EMR data 204 features can include values that represent a hospitalization history for the patient (e.g., time, duration, frequency, etc.). The EMR data 204 features can include values that represent a history of thrombosis for the patient (e.g., frequency, location, and/or severity).

In another example, the EMR data 204 features can be associated with an environmental classifier. The features can include results from the short IBD questionnaire (e.g., an SIBDQ). The features can include values representing a patient diet, such as whether dairy has been consumed. The features can include values representing environmental exposures of the patient, including whether over the counter (OTC) drugs have been consumed by the patient, patient infections (e.g., types, locations, frequencies, etc.), and whether the patient has traveled or undergone major life events that may contribute stress to the patient's life. The features can include values representing relevant family history of disease. The features can include values representing fecal incontinence in the patient in the past. In these examples, values for these features can affect the weightings of a neural network (or other machine learning model) used for generating predictions of disease progression, as subsequently described.

The registry 208 includes patient data across patient populations. The registries can include anonymized health data that relates health trends to particular symptoms, IBD scores, patient phenotypes, and so forth. The registry data 208 can include data representing results for how different treatments for different stages of a disease (such as IBD) affected patients.

The registry data 208 includes clinical trial data 216. The clinical trial data include results and other data from studies, experiments, and clinical trials that test treatment regimens. The treatment regimens can include drug therapy, physical therapy, surgery, or other possible treatments.

The registry data 208 include third party registries 218. The registries 218 can be existing or established databases accessible by subscription or for free. These registries provide large amounts of data for a treatment space such as IBD that can help inform the machine learning module 113, and/or prediction module 116 as to how to score symptoms and to predict how IBD may progress in a patient with particular symptoms or associated with a particular patient history.

The registry data 208 includes claims data 220. The claims data 220 includes billing codes or other standardized data that physicians, pharmacies, hospitals, and other medical service providers submit to payers (e.g., insurance companies, Medicare). Claims data 220 generally includes a standard format across a wide variety of systems. The codes associated with services performed are a standard set of pre-established codes that describe specific diagnoses, procedures, and drugs. Additionally, nearly every encounter that a patient has with the medical system leads to the generation of a claim, creating an abundant and standardized source of patient information. The claims data 208 can be used to determine how patients are generally interacting with healthcare, both at an individual level and across patient populations.

The -omics data 206 includes genetic or molecular profiles of patient populations. The omics data 206 can provide a context as to how a given patient responds to a given treatment. Patients may be grouped by common expressions shown in omics data 206, and the machine learning module 113 and prediction module 116 can generate predictions based on correlations found in the data. Generally, the omics data 206 include genomics, which include a patient genome or genomic data 222. The omics data 206 include proteomics data representing sets of proteins produced by an organism. The omics data 206 include transcriptomics data such as sets of RNA molecules, including mRNA, rRNA, tRNA, and other non-coding RNAs relevant to treatment outcomes. The omics data 206 include pharmacogenomics data representing an effect of variations within the human genome on response to drugs. The omics data represent phenotypic traits, such as comprehensive description of disease symptoms in a patient. Additionally, the omics data 206 can include microbiome data 224 and third party biobank registries 226 including any of the foregoing data. Other omics data 228 can also be included.

In some implementations, the omics data 206 includes data representing features that are used for classifiers for the machine learning models subsequently described. For example, a genomic classifier can be applied to the omics data 206. The -omics data 206 can include feature data having values representing genome sequencing from blood for analysis by the molecular genomics classifier. Other feature data for the molecular genomics classifier can include bisulfite sequencing (RRBS) data from blood of the patient. The -omics data 206 can include feature data having values representing ChIP-sequencing for the patient and/or other patients. The -omics data 206 can include feature data having values representing HLA-DR genotyping for the patient and/or other patients. The -omics data 206 can include feature data having values representing genome sequencing from saliva of the patient.

In another example, a molecular microbiome classifier can be applied to the omics data 206. The -omics data 206 can include feature data having values representing a 16s microbiome sequence from stool of the patient and/or a 16s microbiome sequence from a biopsy of the patient. In some implementations, the -omics data 206 can include feature data having values representing metagenomics, metatranscriptomic information, metabolite profiling results for the patient, and/or virome data associated with the patient.

In another example, a molecular classifier can be applied to the omics data 206. The -omics data 206 can include feature data having values representing epithelial cell profiling from biopsy of the patient and/or single cell assay from a biopsy of the patient.

In another example, a transcriptomics classifier can be applied to the omics data 206. The -omics data 206 can include feature data having values representing a transcriptome sequence from a biopsy of the patient and/or a single-cell RNA sequence from a biopsy of the patient. In some implementations, the data can include proteomics data (e.g., proteomic sequencing) as feature data. In these examples, values for these features can affect the weightings of a neural network (or other machine learning model) used for generating predictions, as subsequently described.

In another example, a laboratory results classifier can be applied to laboratory results from the patient. The results can be included in the -omics data, registry data 208, and/or EMR data 204. The laboratory results data can include feature data having values representing an activity of a blood sample of the patient. The laboratory results data can include feature data having values representing fecal calprotectin or lactoferrin of the patient. The laboratory results data can include feature data having values representing Haematocrit levels for the patient, either at a point in time or over a period of time. The laboratory results data can include feature data having values representing serum CRP/C-reactive protein levels in the patient. The laboratory results data can include feature data having values representing Pharmacokinetics (PK) data associated with a patient (such as in response to a drug therapy). The laboratory results data can include feature data having values representing histology results for the patient. The laboratory results data can include feature data having values representing a full blood analysis of the patient, including values for white blood cell counts (WBC), hemoglobin (HgB), platelets, albumin, creatinine, and/or ESR levels. The laboratory results data can include feature data having values representing a urea analysis of the patient. The laboratory results data can include feature data having values representing liver function tests of the patient. The laboratory results data can include feature data having values representing ferritin, B12, Folate and VitD levels in the patient. The laboratory results data can include feature data having values representing SCFA levels in stool of the patient. The laboratory results data can include feature data having values representing basal metabolite panel in the patient. The laboratory results data can include feature data having values representing one or more tests, such as a fecal lactoferrin test and/or a fecal occult blood test (FOBT). The laboratory results data can include feature data having values representing blood tests to identify perinuclear anti-neutrophil cytoplasmic antibodies (pANCA), anti-*Saccharomyces cerevisiae* antibodies (ASCA), anti_CBir1_antibodies, and/or anti_OmpC_antibodies. In these examples, values for these features can affect the weightings of a neural network (or other machine learning model) used for generating predictions, as subsequently described.

In another example, a symptoms classifier can be applied to symptoms data from the patient. The results can be included in the -omics data, registry data 208, and/or EMR data 204. The symptoms data can include feature data having values representing a number of liquid stool per week for a patient, a bowel frequency for the patient, data representing rectal bleeding in the patient (e.g., frequency and severity), a general well-being of the patient (e.g., from survey data), abdominal pain during a week as reported by the patient, an urgency of defecation reported by the patient, and so forth.

Generally, the gastro data 202, the EMR data 204, the registry data 208, and the omics data 206 are stored as structured data in the centralized IBD data store 201. Features can be extracted from any of the data stored in the data store 201 for use during classification by the machine learning module 113, scoring by a scoring module, or generating predictions from the predictions module 116.

The data from each of sources 202, 204, 206, and 208 are normalized and/or standardized before being stored in the centralized data store 201 (also called the real-world data (RWD) data store). To standardize data, actions are taken to ensure that all fields or values that are used in the machine learning models are populated. If data are missing, the fields can be populated with default values or null values (e.g., those values are discarded in the models). In some implementations, a request is automatically generated to flag missing data to a relevant user. For example, an alert can be generated and sent (e.g., via email) to a patient or physician to complete a form.

For each set of data, specific operations can be performed to normalize and/or standardize that data. For example, video data can be converted to a particular format that is compatible as an input for the machine learning models. The video data can be preprocessed so that frames including bad data (e.g., blocked or dark frames) are removed. Video data can be reduced to a standard length or number of frames. Statistical analyses can be performed to ensure that the video data satisfies one or more data quality metrics, such as comparing the video to color/hue averages of other videos of the video library, etc. In some implementations, forms (such as EMR or EHR) can be checked to ensure all fields are populated before machine learning model analysis is performed. In some implementations, the data processing system ensures that all data received from a particular source has the same units (e.g., size in centimeters or inches, etc.).

Data normalization includes ensuring that data being received by the machine learning model is within expected ranges of values. For example, if demographic data suggests a patient is too young (e.g., negative years old) or too old (e.g., hundreds of years old), a data quality flag can be raised to request correction of the data. This example is illustrative, and other similar checks can be performed. For example, if data received in the timeline are too far apart for correlation between multiple machine learning model outputs for the timeline, the data processing system 100 can indicate that additional data are needed. More specifically, if the time period between two observations or measurements of patient data is too long, the data processing system can indicate a lower likelihood of correlation or confidence or request additional data.

Figure 2B:
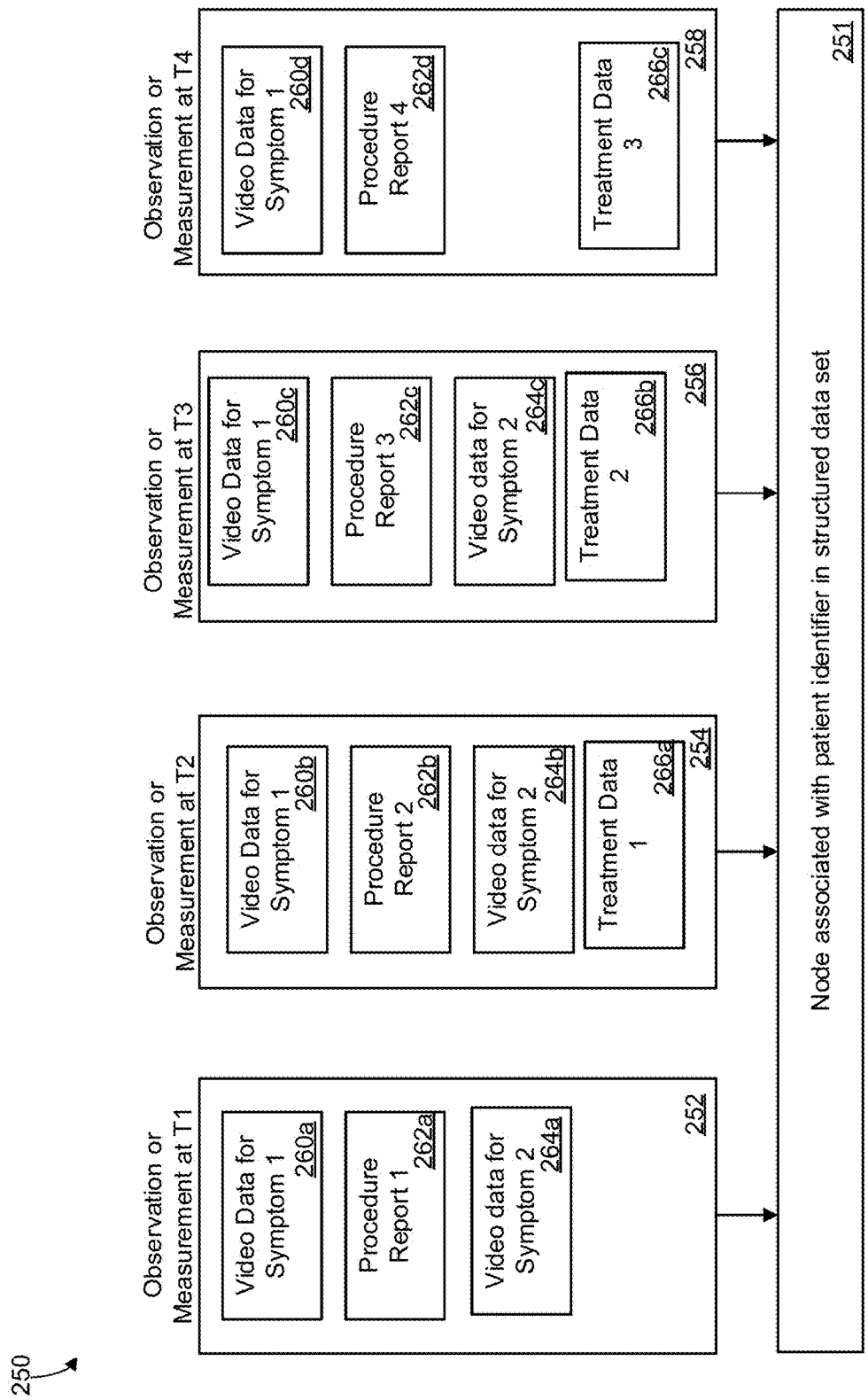
FIG. 2B shows a record of real world data (RWD) for a patient for a timeline at a node storing a structured dataset.

FIG. 2B shows a record 250 of real world data (RWD) for a patient for a timeline. The record 250 is stored in a node 251 configured to store a structured dataset. The data entries 252, 254, 256, and 258 each correspond to a measurement or observation of a common patient associated with the record 250. The patient can be associated with an identifier that identifies the node 251 so that additional entries of the patient record (e.g., for additional measurements in the timeline) are stored in the node 251 and associated with the record 250.

The example record 250 includes four entries 252, 254, 256, and 258, each corresponding to a point in time for the patient treatment. In some implementations, each point in time corresponds to when additional data on the patient is acquired (e.g., by an endoscopy or other doctor visit). However, the timeline need not be related to a doctor visit. The timeline can be updated whenever additional data are added for the patient that correspond to a new time in the timeline (e.g., if the patient completes a survey indicating a status of his symptoms for a particular point in time). Any of the data of data store 201 can be included in the node 251.

In the example record 250, the first entry 252 corresponding to an initial point in time T1 includes endoscopy data (e.g., video data). The video data has two features, each corresponding to a respective tracked symptom 260, 264. Here, the data refers to a state 260a, 264a of each symptom at the initial time T1. In some implementations, these features are combined into a single instance of data in the entry 252. A procedure report 262a is included to detail what endoscopy was performed at T1 (e.g., what location, how long the procedure was, what tools were used, and other relevant data).

A second entry 254 corresponds to a second time point T2 in the timeline. The second entry can be created at any point in time T2 after the initial point in time T1. This can be days, weeks, months, or years later, for example. The entry 254 includes updates for each of the first and second symptoms identified at T1. For example, video data 260b corresponds to symptom 1 (e.g., inflammation at location 1) of data 260a of T1. Additionally, video data 264b of symptom 2 (e.g., inflammation at location 2) corresponds to data 264a of T1. A new procedure report 262b is generated for the second observation data of entry 254. Additionally, treatment data 266a is included specifying what treatment occurred from T1 to T2. This treatment data 266a can be related to outcomes at T2, and used to predict future outputs at point T3 and or recommend new treatment.

A third entry 256 corresponds to a third time point T3 in the timeline. The third entry can be created at any point in time T3 after the second point in time T2. The entry 256 includes updates for each of the first and second symptoms identified at T1 and T2, and any new symptoms if applicable. For example, video data 260c corresponds to symptom 1 (e.g., inflammation at location 1) of data 260a of T1 and 260b of T2. Additionally, video data 264c of symptom 2 (e.g., inflammation at location 2) corresponds to data 264a of T1 and 264b of T2. A new procedure report 262c is generated for the second observation data of entry 256. Additionally, treatment data 266b is included specifying what treatment occurred from T2 to T3. This treatment data 266a can be related to outcomes at T3, and used to predict future outputs at point T4 and/or recommend new treatment if the first treatment was ineffective or effective enough to require lower drug dosages, for example.

A fourth entry 258 corresponds to a fourth time point T4 in the timeline. The fourth entry 258 can be created at any point in time T4 after the third point in time T3. The fourth entry 258 includes updates for each of the first and second symptoms identified at T1, T2, and T3, and any new symptoms if applicable. For example, video data 260c corresponds to symptom 1 (e.g., inflammation at location 1) of data 260a of T1, 260b of T2, and 260c of T3. Symptom 2 (e.g., inflammation at location 2) has disappeared, so there is no longer data corresponding to data 264a of T1, 264b of T2, and 264c of T3. A new procedure report 262c is generated for the second observation data of entry 256. Additionally, treatment data 266c is included specifying what treatment occurred from T3 to T4. This treatment data 266a can be related to outcomes at T4, and used to predict future outputs as previously described.

As subsequently described, a machine learning model can be associated with each corresponding data source over the timeline, such as video data 260 for symptom 1, video data 264 for symptom 2, procedure data 262, and treatment data 266. In some implementations, the video data 260, 264 for multiple symptoms can be analyzed in a common machine learning model. Each of these machine learning models is combined into a global model for generation of final predictions to relate each of the sources 260, 262, 264, and 266 of the timeline of record 250.

As subsequently described, each entry 252, 254, 256, and 258 can be associated with the IBD severity score indicating the severity of the disease at the respective point in time T1, T2, T3, and T4. This scoring data are included in the record 250 for use in predicting future disease severity (e.g., using at least one of the scores, but typically two or more of the scores).

Figure 3:
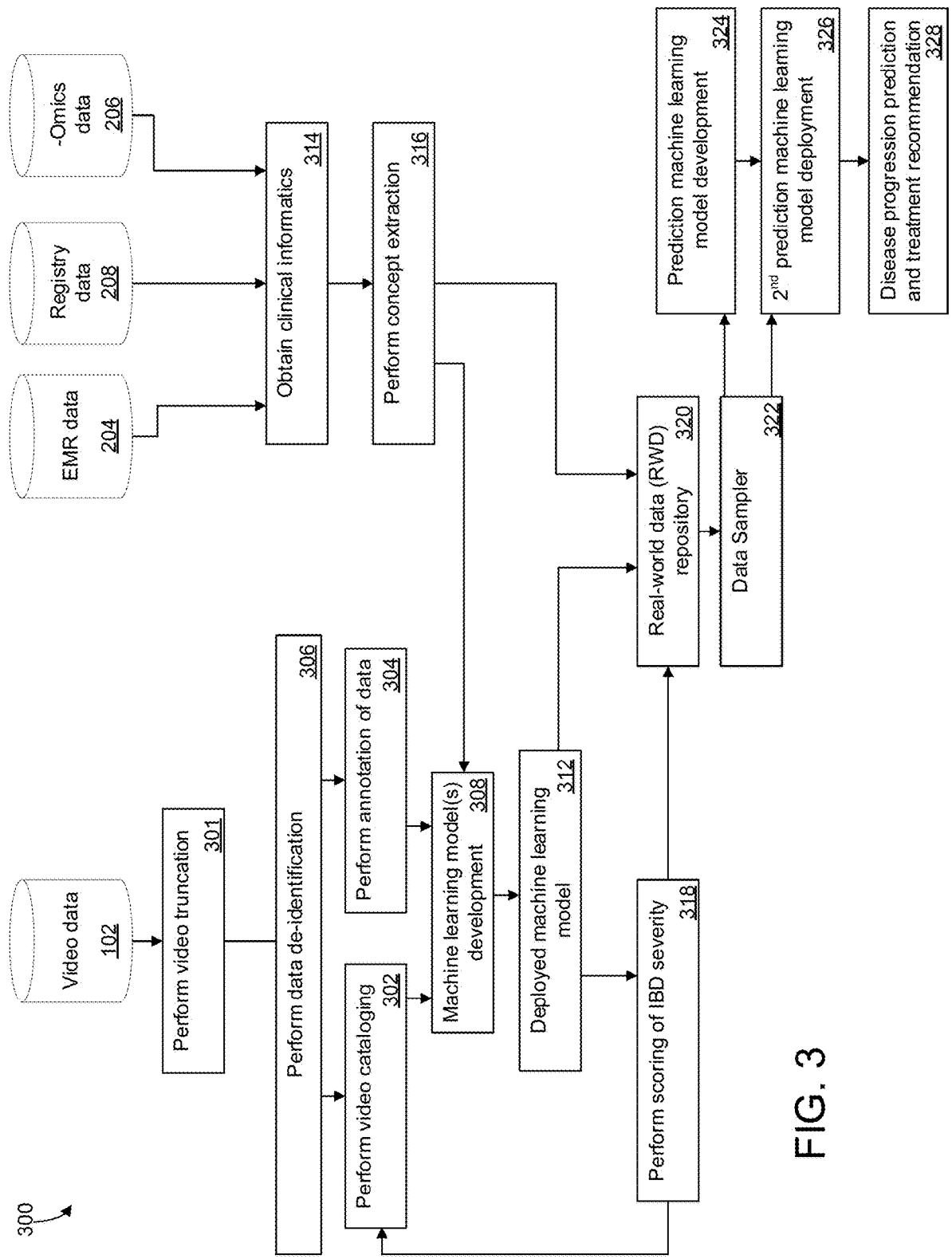
FIG. 3 shows examples of data processes for training and developing machine learning models for prediction of an IBD disease score and then a prediction of IBD progression and treatment outcomes.

FIG. 3 shows examples of data processes 300 for training and developing machine learning models for prediction of each of IBD severity and treatment outcomes (e.g., by machine learning module 113 of FIG. 1). The process 300 includes receiving video data 102, EMR data 204, registry data 208, and omics data 206. While these data 102, 204, 206, and 208 are specifically discussed, other data (as previously described) can be incorporated into the machine learning model.

The machine learning module 113 is configured to perform (301) video truncation to extract video data for processing. Truncation can include removing portions of the video data that are not relevant to the scoring process because the portions do not include relevant data, include redundant data, or include data that is noisy or otherwise unusable (e.g., image frames that are out of focus, not illuminated, and so forth).

The machine learning module 113 is configured to de-identify (306) the video data. This can include data masking, anonymization, data scrambling, removal of portions of the data, and so forth. In some implementations, the de-identification of the video data can be performed by another module or system besides the machine learning model 113. For example, the de-identification of the data can be performed by an interfacing module before any data are processed by the machine learning model 113. In another example, the de-identification of the data can be performed prior to storage of the data 102, so that data accessed the data processing system are already anonymized.

The machine learning module 113 is configured to perform (302) video cataloging. This includes structuring the video data 102 based on metadata associated with the video data. The metadata may be generated when the video data are generated, or can be associated with the video data during cataloging. The metadata may include identifications of an operation associated with the video data 102, a timestamp, and so forth.

The machine learning module 113 is configured to perform (304) annotation of the video data 102. The annotation is based on image processing of the video. Annotations can be associated with each video frame, or with portions of the video clip. This can provide both frame-level data, which includes annotations associated with individual frames of the video data 102. Frame level annotations can include data relevant to a particular frame. For example, the frame level annotations may include data represented whether bleeding is observed, a number of polyps, in the image, and/or a location in the tract associated with the particular image frame. The annotations are also case level annotations, which include annotations describing entire videos including multiple image frames. The case level annotations include information about the video overall, such as aggregates of annotations stored with individual frames. This can include annotations indicating that, for example, bleeding was observed a particular number of times in the video, or not at all. In another example, a total number of polyps that were observed can be included in the case level annotations. In another example, a percentage of frames including polyps, bleeding, neither, or both can be included in the annotations. Other such annotations can be included at the case level.

After de-identification, the machine learning module 113 is further developed (308) based on receiving data from the additional sources 103, such as EMR data 104, registry data 208, and omics data 206. The machine learning module 113 obtains (314) clinical informatics for each of these data sources. This can include structuring the data (e.g., in the centralized database 201 of FIG. 2). In some implementations, the informatics are obtained by identifying an existing structure for the data 204, 206, and 208. In some implementations, the process 300 includes feature extraction (316) from these data by the machine learning module 113. These data 104, 106, 108 are also de-identified (306) for use in the machine learning model. These data can also be stored (320) as real world data (RWD) in a database. This database can be used for one or more downstream applications (326).

The scores and predictions stored in repository 320 are normalized and standardized in a similar manner as the data of each of sources 102, 202, 204, 206, and 208, as previously described. For example, the output score of each machine learning model can be standardized to be between 0-1. In some implementations, the output of each machine learning model is adjusted to a common format for the global machine learning model, as subsequently described.

The machine learning module 113 is developed (308) using one or more of the data 102, 204, 206, and 208, as subsequently described. The machine learning module 113 can include, for example, a trained classifier, convolutional neural network, recurrent neural network, support vector machine, or other such machine learning model. The machine learning module 113 is configured to train the model using one or more of the data 102, 204, 206, and 208.

The process 300 includes deploying (312), by the machine learning module 113, the machine learning model that is trained. The machine learning module 113 is configured to perform endo-grading (318) of the video data 102 based on the trained machine learning model. This process includes a composite score analysis. When more than one machine learning model is used to analyze the video data 102, the scores generated by each of the models are combined into a composite score. The combination process can be a voting system, a weighted average, or a similar process. The composite score can be determined from multiple frame scores such that a composite score is developed for each frame. In some implementations, a composite score is developed for each video based on a combination composite frame scores or based on a combination of video scores from each of the models. In some implementations, each frame of the video can be associated with a respective prediction value. The data processing system 100 is configured to arbitrate the various prediction values into a clip score for the particular symptom or location of the patient.

The score is then normalized and also stored in the RWD 320. Next, an algorithm 321 will sample at least one but potentially all of the data sources that have been normalized and stored in the RWD 320 and analysis the same data set across at least three different time periods. This information will then be used for machine learning model development 324 where clustering and other techniques are used to start predicting for the third time frame. Once the model is trained, the machine learning model will be deployed 326 at which point the data sampler 322 only needs to select at least one data source (but could be all or some of the data sources) across at least two distinct time frames and use that to predict disease severity and treatment recommendations 328 at a third, later time frame. The scoring/endo-grading 318 can be an input to the RWD that is used for generation of the machine learning model 324. For example, similar to other data modalities, the IBD severity score at each time period (showing the disease severity at that time) is used as a feature or input to the machine learning model 324.

Figure 4:
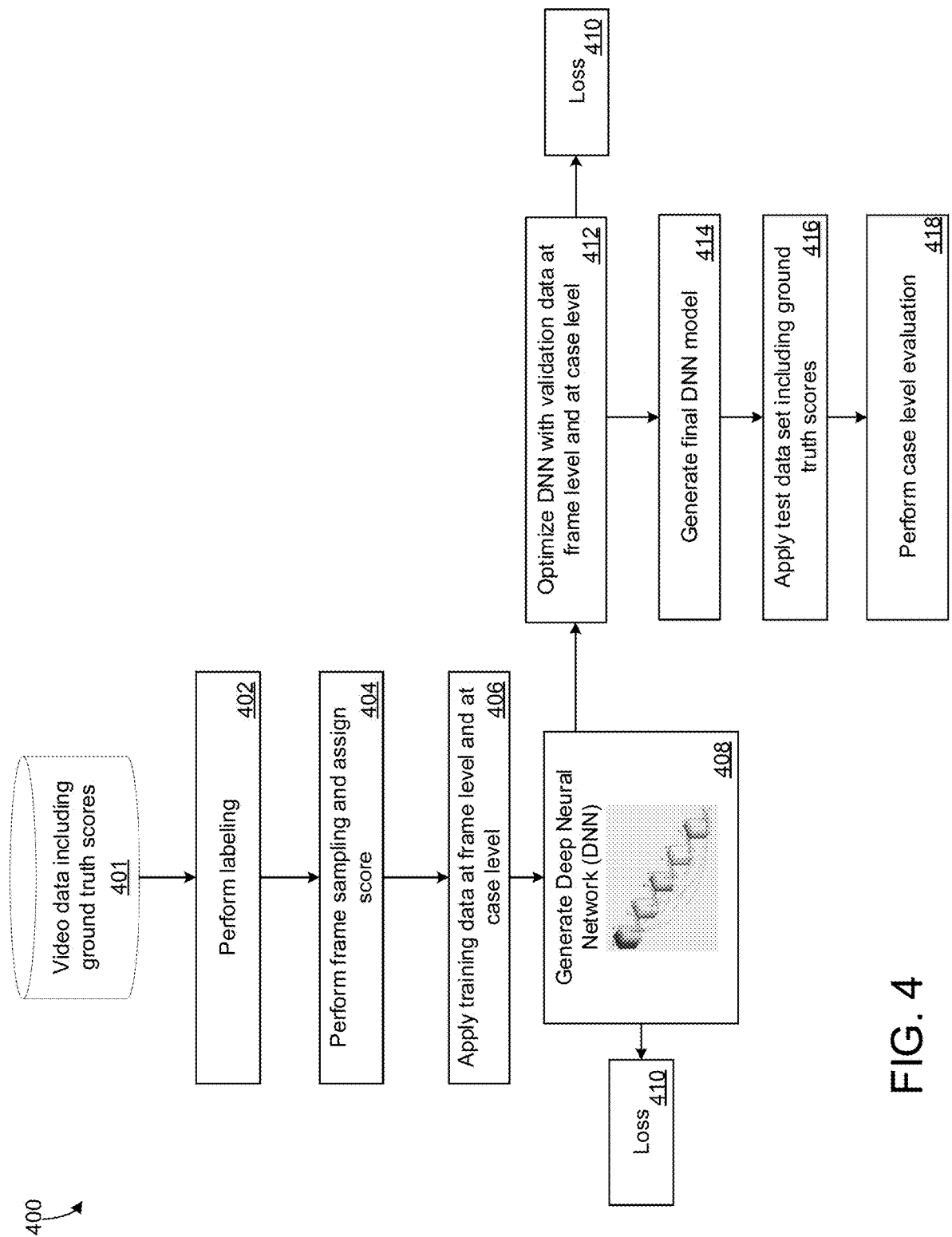
FIG. 4 shows an example flow diagram for performing automated regression or classification analysis for prediction of IBD score/activity.

FIG. 4 shows an example flow diagram of a process 400 for performing automated regression or classification analysis for detection of IBD (e.g., by the machine learning module 113 of FIG. 1). For the machine learning algorithm to be able to predict outcomes from the data from previous time frames, a classical regression, a multivariate regression, or a supervised MLK algorithm involving multiple data variables can be included in the machine learning module 113. In some implementations, separate models are included for each clinical variable and for the score derived from visual colonoscopy data in order to determine how each model performs in tandem and with other variables, as previously described.

The process 400 includes applying training data 406 to train a machine learning model 408 (such as a model of module 113 of FIG. 1). The training data can include data with either or both frame level annotations and case level annotations. The model 408 of the machine learning module 113 is trained using the training data 406 generated from the frame sampled data. Weight values and activation values are tuned for the machine learning model 408, which can be a deep neural network (DNN) or other similar model. Loss values 410 are generated. A loss value 410 represents a penalty for a bad score and can be used to optimize (412) the model 408 until loss values approach zero.

The model 408 is optimized using validation data. The validation data further refine the model 408. The validation data generally include "new" data that are annotated with either or both frame level annotations and case level annotations. The validation data are used to ensure that the model 408 is outputting expected results based on the annotated data being processed by the model 408. The model 408 is refined until a final model 414 results, where the final model is a validated model.

The validated model 414 is executed (416) on a test data set to evaluate outcomes of the model 414. The test data are pristine, non-annotated data that have not yet been processed by the model 414. The test data are processed using the established ground truth scores of the model 414. Generally, the test data are used to perform (418) case level evaluation of the model 414. The validation dataset can include known classifications or other data that indicate a classification or otherwise train the machine learning model. A test dataset can also be applied which includes pristine, unannotated data to test the model 414. The test dataset can be manually evaluated to determine whether the model 414 is operating as intended with unseen data.

The data previously described is obtained and used in the process 400 to generate the classifiers that were previously described. These classifiers can be used individually and/or in combination to generate score data for the patient. For example, the gastro data 202, the EMR data 204 registry data 208 and/or the -omics data 206 previously described are used to train, validate, and test one or more classifiers. The classifiers can include, as previously described, a concomitant medications classifier, a demographic classifier, an endoscopy classifier, an environmental classifier, a genomics classifier, a laboratory results classifier, a microbiome classifier, a patient medical history classifier, a physical examination classifier, a proteomics classifier, a symptoms classifier, and/or a transcriptomics classifier, or any combination thereof.

In some implementations, the above described classifiers can be combined to generate the score for IBD for a patient. In some implementations, a statistical combination of the classifier outputs can be used. For example, these can include combining the outputs of the classifiers based on a function of each output of the classifiers. For example, the function can include a weighted average, a voting system, a ratio, or some other combination of the classifier output values. In some implementations, the classifier outputs can be combined into an input vector for another machine learning model that receives the classifier outputs as input values. This can be called a second order machine learning model. The second order machine learning model can include any of the machine learning models previously or subsequently described. Additionally, the second order machine learning model can be trained with example classifier outputs in a similar manner as previously described for the machine learning models of the classifiers.

In some implementations, the model 414 includes a convolutional neural network (CNN). A convolutional neural network (CNN) can be configured based on a presumption that inputs to the neural network correspond to image pixel data for an image or other data that includes features at multiple spatial locations. For example, sets of inputs can form a multi-dimensional data structure, such as a tensor, that represent color features of an example digital image (e.g., an image of the surroundings of a vehicle). In some implementations, inputs to the neural network correspond to a variety of other types of data, such as data obtained from different devices and sensors of a vehicle, point cloud data, audio data that includes certain features or raw audio at each of multiple time steps, or various types of one-dimensional or multiple dimensional data. A convolutional layer of the convolutional neural network can process the inputs to transform features of the image that are represented by inputs of the data structure. For example, the inputs are processed by performing dot product operations using input data along a given dimension of the data structure and a set of parameters for the convolutional layer.

Performing computations for a convolutional layer can include applying one or more sets of kernels to portions of inputs in the data structure. The manner in which a system performs the computations can be based on specific properties for each layer of an example multi-layer neural network or deep neural network that supports deep neural net workloads. A deep neural network can include one or more convolutional towers (or layers) along with other computational layers. In particular, for example computer vision applications, these convolutional towers often account for a large proportion of the inference calculations that are performed. Convolutional layers of a CNN can have sets of artificial neurons that are arranged in three dimensions, a width dimension, a height dimension, and a depth dimension. The depth dimension corresponds to a third dimension of an input or activation volume and can represent respective color channels of an image. For example, input images can form an input volume of data (e.g., activations), and the volume has dimensions 32×32×3 (width, height, depth respectively). A depth dimension of 3 can correspond to the RGB color channels of red (R), green (G), and blue (B).

In general, layers of a CNN are configured to transform the three dimensional input volume (inputs) to a multi-dimensional output volume of neuron activations (activations). For example, a 3D input structure of 32×32×3 holds the raw pixel values of an example image, in this case an image of width 32, height 32, and with three color channels, R-G-B. A convolutional layer of a neural network of the model 414 computes the output of neurons that may be connected to local regions in the input volume. Each neuron in the convolutional layer can be connected only to a local region in the input volume spatially, but to the full depth (e.g., all color channels) of the input volume. For a set of neurons at the convolutional layer, the layer computes a dot product between the parameters (weights) for the neurons and a certain region in the input volume to which the neurons are connected. This computation may result in a volume such as 32×32×12, where 12 corresponds to a number of kernels that are used for the computation. A neuron's connection to inputs of a region can have a spatial extent along the depth axis that is equal to the depth of the input volume. The spatial extent corresponds to spatial dimensions (e.g., x and y dimensions) of a kernel.

A set of kernels can have spatial characteristics that include a width and a height and that extends through a depth of the input volume. Each set of kernels for the layer is applied to one or more sets of inputs provided to the layer. That is, for each kernel or set of kernels, the model 414 can overlay the kernel, which can be represented multi-dimensionally, over a first portion of layer inputs (e.g., that form an input volume or input tensor), which can be represented multi-dimensionally. For example, a set of kernels for a first layer of a CNN may have size 5×5×3×16, corresponding to a width of 5 pixels, a height of 5 pixel, a depth of 3 that corresponds to the color channels of the input volume to which to a kernel is being applied, and an output dimension of 16 that corresponds to a number of output channels. In this context, the set of kernels includes 16 kernels so that an output of the convolution has a depth dimension of 16.

The model 414 is configured to compute, when executed by the machine learning module 113, a dot product from the overlapped elements. For example, the model 414, by the machine learning module 113, is configured to convolve (or slide) each kernel across the width and height of the input volume and compute dot products between the entries of the kernel and inputs for a position or region of the image. Each output value in a convolution output is the result of a dot product between a kernel and some set of inputs from an example input tensor. The dot product can result in a convolution output that corresponds to a single layer input, e.g., an activation element that has an upper-left position in the overlapped multi-dimensional space. As discussed above, a neuron of a convolutional layer can be connected to a region of the input volume that includes multiple inputs. The model 414, by the machine learning module 113 convolves each kernel over each input of an input volume. The model 414, by the machine learning module 113, performs this convolution operation by, for example, moving (or sliding) each kernel over each input in the region.

The model 414, by the machine learning module 113, moves each kernel over inputs of the region based on a stride value for a given convolutional layer. For example, when the stride is set to 1, then the model 414 moves the kernels over the region one pixel (or input) at a time. Likewise, when the stride is 2, then the model 414 moves the kernels over the region two pixels at a time. Thus, kernels may be shifted based on a stride value for a layer and the model 414 can repeatedly perform this process until inputs for the region have a corresponding dot product. Related to the stride value is a skip value. The skip value can identify one or more sets of inputs (2×2), in a region of the input volume, that are skipped when inputs are loaded for processing at a neural network layer. In some implementations, an input volume of pixels for an image can be "padded" with zeros, e.g., around a border region of an image. This zero-padding is used to control the spatial size of the output volumes.

As discussed previously, a convolutional layer of CNN is configured to transform a three dimensional input volume (inputs of the region) to a multi-dimensional output volume of neuron activations. For example, as the kernel is convolved over the width and height of the input volume, the model 414 produces a multi-dimensional activation map that includes results of convolving the kernel at one or more spatial positions based on the stride value. In some cases, increasing the stride value produces smaller output volumes of activations spatially. In some implementations, an activation can be applied to outputs of the convolution before the outputs are sent to a subsequent layer of the neural network.

An example convolutional layer can have one or more control parameters for the layer that represent properties of the layer. For example, the control parameters can include a number of kernels, K, the spatial extent of the kernels, F, the stride (or skip), S, and the amount of zero padding, P. Numerical values for these parameters, the inputs to the layer, and the parameter values of the kernel for the layer shape the computations that occur at the layer and the size of the output volume for the layer. In one implementation, the spatial size of the output volume is computed as a function of the input volume size, W, using the formula (W?F+2P)/S+1. For example, an input tensor can represent a pixel input volume of size [227×227×3]. A convolutional layer of a neural network can have a spatial extent value of F=11, a stride value of S=4, and no zero-padding (P=0). Using the above formula and a layer kernel quantity of K=96, the model 414 performs computations for the layer that results in a convolutional layer output volume of size [55×55×96], where 55 is obtained from [(227−11+0)/4+1=55].

The computations (e.g., dot product computations) for a convolutional layer, or other layers, of a neural network involve performing mathematical operations, e.g., multiplication and addition, using a computation unit of a hardware circuit of the model 414. The design of a hardware circuit can cause a system to be limited in its ability to fully utilize computing cells of the circuit when performing computations for layers of a neural network.

Based on the aforementioned techniques, the model 414 is configured to identify locations of potential malignancies in images. In some implementations, potential malignancies include polyps. In some implementations, given a set of images, the model 414 is capable of correctly detecting at least 87% of all polyps shown (e.g., at least one image of at least 87% of the polyps presented in the set of images will be correctly detected and identified). In some implementations, when given a set of images, and the model 414 is capable of making a determination that an image does not contain a polyp, and that determination is correct at least 98.7% of the time (e.g., it is likely to be correct 98.7% of the times the machine learning 113 system makes a "does not contain polyp" classification).

In some implementations, the model 414 includes other types of digital neural networks, such as a recurrent neural network (RNN), a radial basis function network, a deconvolution network, a variational auto-encoder (VAE), generative adversarial network (GAN) and so forth.

Figure 5:
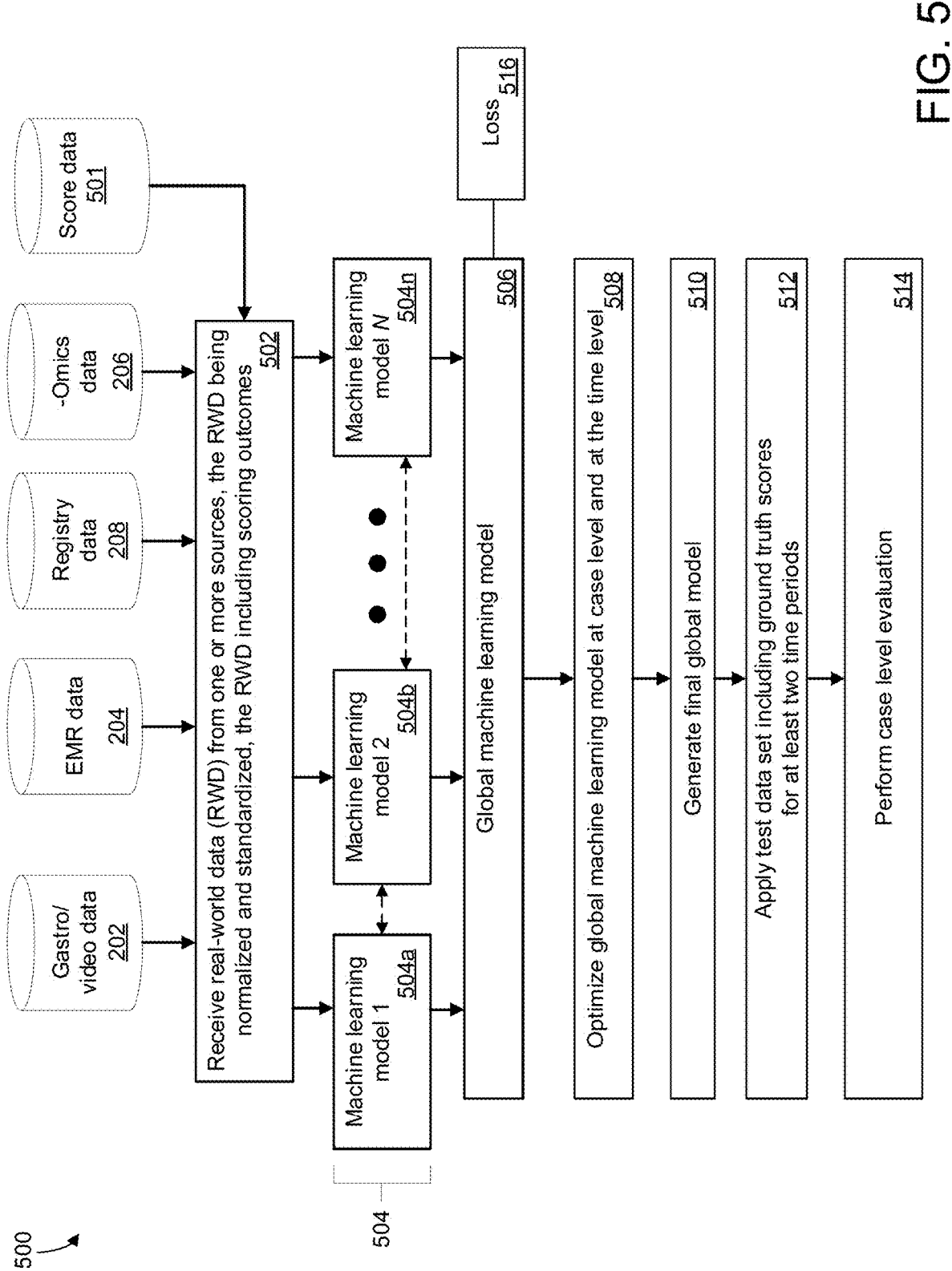
FIG. 5 shows an example system including a plurality of machine learning models for generating predictions of disease outcomes and disease progression for treating IBD.

FIG. 5 shows a flow diagram showing a process 500 for prediction of disease progression for IBD, and recommending one or more treatments for IBD based on data sources 202, 204, 206, and 208 and scoring data 501 performed from scoring IBD severity (or other disease severity).). Generally, once the standardized and/or normalized data of each of the sources 202, 204, 206, 208, and 501 are received, the data processing system 100 selects some or all of the data (e.g., data 103 and scoring data 501) from a plurality of time points (e.g., generally three or more time points). The data from each of the time points correspond to observations or measurements for a particular patient at a particular region or location (or for a particular symptom). The observations or measurements are associated with one another in the RWS data store 201, such as with in index or other structured data set. For example, each patient can be represented by a node in structured data set. The node stores an index value representing the patient. The node stores data for each observation or measurement for the patient for each location, symptom, etc. of the patient. Each tracked symptom or disease is correlated to other measurements or observations for that patient in a respective patient timeline. In this way, the progression of disease symptoms is tracked for the patient. When the data are sent to the machine learning model(s), each instance representing the observation or measurement on the timeline corresponds to a feature input into the respective model.

The data processing system includes a plurality of machine learning models 504 (shown as models 504a-n) to analyze respective data types 202, 204, 206, 208, 501, or sub portions of data from these data types. For example, a first model 504a is configured to analyze a timeline of feature data for detected inflammation in video data. A second model 504b is configured to analyze growth or shrinkage of a polyp. A third model 504n is configured to track patient responses of pain felt or other outcome metrics. Additional machine learning models of models 504 are each configured to track a specific symptom or other data gathered at each observation or measurement of a patient for the patient's timeline. Each of the machine learning models 504a-n generates an output score or result.

In some implementations, the data processing system applies training and analysis for each data source selected (i.e. omics, EMR/EHR, scoring) using either classic regression, multivariable regression, supervised MLK algorithms to predict outcomes from each of the data sources. Each of the outputs of the machine learning models 504 are combined into a global model 506 that could uses one or more of Bayesian models, Markov models, linear mixed models, clustering analysis (such as principle component analysis), or a combination of any or all of those models, to general a final outcome. For example, the output scores for each of the models 504 can be specified as features for the global model 506.

The results of the global model are optimized and a final model is generated by the data processing system. This process is similar to that of generating the scoring model as described in relation to FIG. 4. The process 500 includes applying training data to train the machine learning model 506. Weight values and activation values are tuned for the machine learning model 506, which can be a Bayesian models, Markov models, linear mixed models, clustering analysis (such as principle component analysis), a similar model, or a combination of any or all of those models. Loss values 516 are generated. A loss value 516 represents a penalty for a bad score and can be used to optimize (508) the model 506 until loss values approach zero.

The model 506 is optimized using validation data. The validation data further refine the model 506. The validation data generally include "new" data that are annotated with either or both frame level annotations and case level annotations. The validation data are used to ensure that the model 506 is outputting expected results based on the annotated data being processed by the model 506. The model 506 is refined until a final model 510 results, where the final model is a validated model.

The validated model 414 is applied (512) on a test data (e.g., ground truth data for two or more periods) to evaluate outcomes of the model 510. The test data are pristine, non-annotated data that have not yet been processed by the model 510. The test data are processed using the established ground truth scores of the model 510. Generally, the test data are used to perform (514) case level evaluation of the model 510. The validation dataset can include known classifications or other data that indicate a classification or otherwise train the machine learning model. A test dataset can also be applied which includes pristine, unannotated data to test the model 510. The test dataset can be manually evaluated to determine whether the model 510 is operating as intended with unseen data. For the final model 510, some or all sources of the data 202, 204, 206, 208, and 501 across at least two time periods are inputted to the final model 510. The model 510 predicts disease progression (e.g., at a third time period after the two used time periods as inputs). In some implementations, the prediction is associated with a recommended treatment changes. The time periods can be set to most any length, but generally include periods of 1 week, 2 weeks, 3 weeks or up to 6 months. In some implementations, the time period can be 1 year or more.

The recommended treatments are based on a comparison of the projected progression with a current treatment that the patient is experiencing. For example, a patient is receiving a drug dosage of a first amount, and the machine learning model 510 predicts that symptoms will worsen but that the drug has been effective in reducing severity thus far. The machine learning model 510 may generate a recommendation to increase a dosage of the effective drug. In another example, the drug dosage has been increased over the previous two periods, and no improvement is predicted. The machine learning model 510 can recommend a different drug be used for treatment. In some implementations, the prediction can include resolution of the symptoms within a threshold severity (e.g., below a given severity). In this example, the machine learning model 510 recommends no change to treatment.

Figure 6:
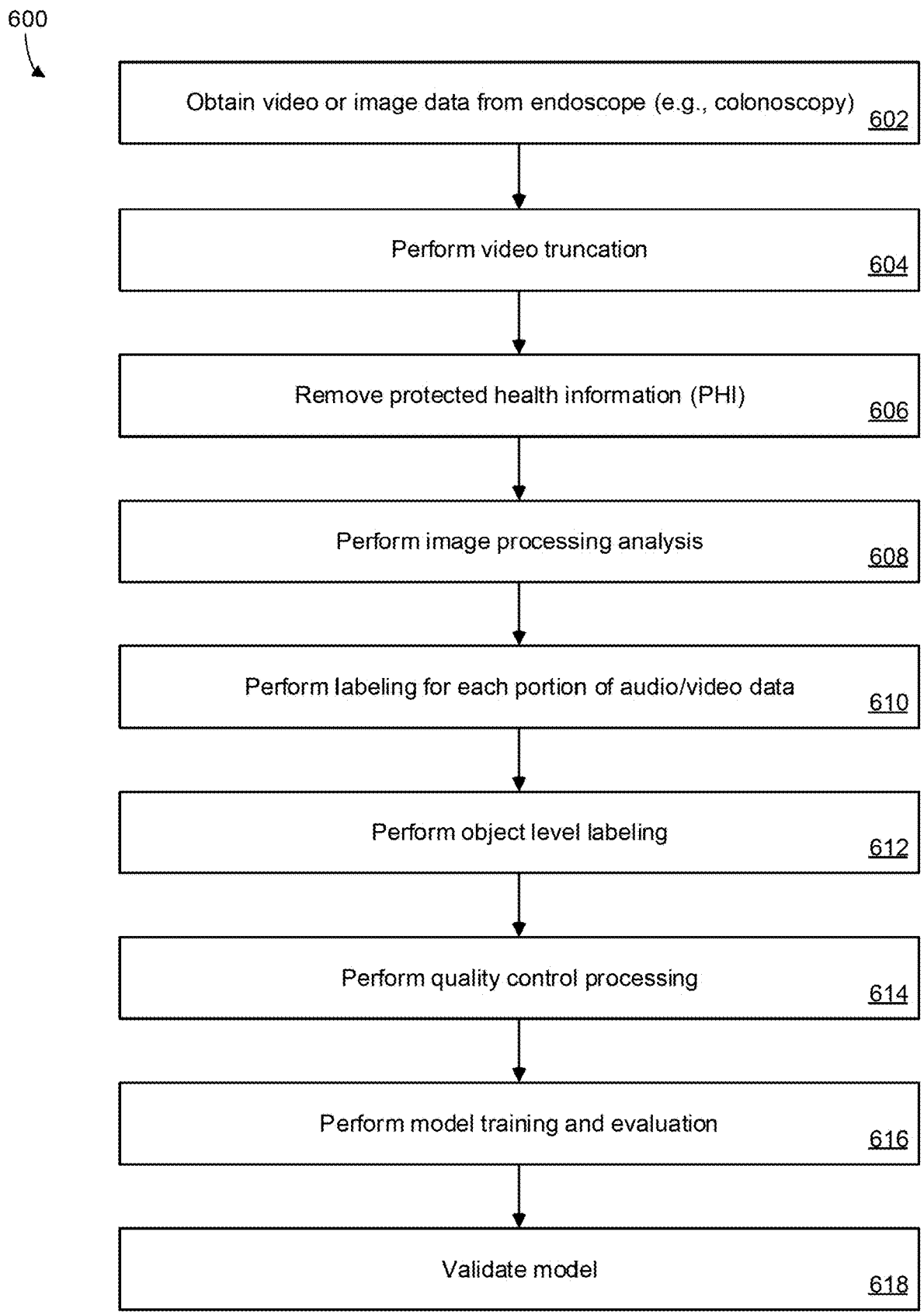
FIG. 6 shows an example flow diagram for a multi-pronged ML process for predicting a score categorizing IBD activity.

FIG. 6 shows a flow diagram showing a process 600 for scoring IBD. The process 600 includes obtaining (602) video or image data from endoscope (e.g., colonoscopy). The process 600 includes performing truncation (604) of the video or image data. The process 600 includes performing (606) an image processing analysis. The process 600 includes removing (608) personally identifying information, such as protected health information (PHI). The process 600 includes performing labeling (610) for each portion of audio/video data. The process 600 includes performing (612) object level labeling. The process 600 includes performing quality control processing (614). The process 600 includes performing model training and evaluation (616). The process 600 includes validating (618) the model. In some implementations, the process 600 includes receiving, from an imaging device, medical images that include endoscopy data. The process 600 includes applying a machine learning model to the medical images to determine one or more measurements of inflammation or other physical characteristic related to IBD. The machine learning model combines image classification with detection bounding boxes and segmentation pixel-wise masks. The process 600 includes determining one or more features to extract from the image data, the features each representing a physical parameter of the GI tract for each of the first time period and the second time period. The process 600 includes extracting the one or more features from the image data to form a first feature vector for the first time period and a second feature vector for the second time period. The process 600 includes selecting a machine learning model based on the one or more features included in the first feature vector and the second feature vector. The process includes processing the first feature vector and the second feature vector using the machine learning model, the machine learning model being trained with labeled image data representing instances of symptoms of IBD being in the GI tract, the labeled image data associating scores representing a progression of IBD based on the respective instances of the symptoms in the first and second vectors. The process 600 includes determining, based on the processing, a prediction of disease progression of IBD in the patient. The process 600 includes storing, in a data store, the prediction in association with the image data.

The process 600 includes obtaining electronic health data of patient. The process 600 includes combining the electronic health data of patient onto the one or more measurements of inflammation including the bounding boxes and pixel-wise masks. The process 600 includes generating, based on the combining, a score indicative of a progression of IBD in the patent. The process 600 includes generating an output that indicates prediction severity of IBD in the patient.

While this specification includes many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

In some implementations, determining the prediction includes determining one or more frame level annotations corresponding to individual frames of a video of the image data; determining one or more case level annotations for the video of the image data; and determining, based on the one or more frame level annotations and the one or more case level annotations, the score associated with the video of the image data.

In some implementations, the one or more features comprise values representing at least one of: a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal; and wherein the prediction representing a severity of IBD in the patient is based on the values of the one or more features.

In some implementations, process 600 includes receiving electronic medical records (EMR) data for the patient, the EMR data including medical information about the patient, wherein the machine learning model is trained with labeled EMR data associating values of medical information of patients with respective severity of IBD in the patients; extracting one or more values from the EMR data to form an EMR feature vector; processing, by the machine learning model or by a second machine learning model in addition to the machine learning model, the EMR feature vector; and generating an updated score representing the severity of IBD in the patient indicated by the EMR data.

In some implementations, the one or more features of the EMR feature vector comprise values representing at least one of: an age of the patient, a sex of the patient, a reproductive history of the patient, a smoking status of the patient, a race or ethnicity of the patient, a presence or absence of an anal fissure in the patient, a fistula or abscess in the patient, and the presence or absence of one or more complications such as uveitis, pyoderma gangernosum, erythema nodosum, and/or arthralgia in the patient, serological profiling results of the patient, a history of medications prescribed to the patient, a history of surgery for the patient, a degree of induration for the patient, a presence or size of an abdominal mass in the patient, a history of flaring in the patient, a hospitalization history for the patient, and a history of thrombosis for the patient.

In some implementations, the process includes receiving registry data for the patient, the registry data including patient data across patient populations, wherein the machine learning model is trained with labeled registry data associating values of for patient populations with respective severity of IBD in particular patients of the patient populations; extracting one or more values from the registry data to form a registry feature vector; processing, by the machine learning model or by a second machine learning model in addition to the machine learning model, the registry feature vector; and generating an updated prediction representing the severity of IBD in the patient indicated by the registry data or a or treatment recommendation for the patient. In some implementations, the one or more features of the registry feature vector comprise values representing at least one of: results and other data from studies, experiments, and clinical trials that test treatment regimens that are associated with the patient including one or more of drug therapy, physical therapy, or surgery, specific diagnoses associated with the patient, procedures, and application of drugs associated with the patient.

In some implementations, the process 600 includes receiving omics data for the patient, the omics data including genetic or molecular profiles of patient populations, wherein the machine learning model is trained with labeled omics data associating values of genetic or molecular profiles with respective severity of IBD in the patients of the patient populations; extracting one or more values from the omics data to form an omics feature vector; processing, by the machine learning model or by a second machine learning model in addition to the machine learning model, the omics feature vector; and generating an updated prediction for the severity of IBD in the patient indicated by the omics data or a treatment recommendation for the patient.

In some implementations, the one or more features of the omics feature vector comprise values representing at least one of: transcriptomics data such as sets of RNA molecules, including mRNA, rRNA, tRNA, and other non-coding RNAs relevant to treatment outcomes; one or more phenotypic traits of the patient; microbiome data for the patient; genome sequencing for the patient; bisulfite sequencing (RRBS) data of the patient; ChIP-sequencing for the patient; HLA-DR genotyping for the patient; a 16s microbiome sequence from stool of the patient; a 16s microbiome sequence from a biopsy of the patient; epithelial cell profiling from biopsy of the patient; a single cell assay from a biopsy of the patient; a single-cell RNA sequence from a biopsy of the patient; fecal calprotectin or lactoferrin of the patient; Haematocrit levels for the patient; serum CRP/C-reactive protein levels in the patient; Pharmacokinetics (PK) data associated with a patient; white blood cell counts (WBC), hemoglobin (HgB), platelets, albumin, creatinine, and/or ESR levels of the patient; a urea analysis of the patient; liver function tests of the patient; ferritin, B12, Folate and/or VitD levels in the patient; SCFA levels in stool of the patient; and basal metabolite panel in the patient.

In some implementations, the machine learning model comprises a convolutional neural network (CNN) or other models, and wherein the each of the instances of symptoms of IBD contributes to an activation value for inputting into a layer of the CNN.

In some implementations, processing the feature vector comprises performing a classification with detection bounding boxes and segmentation pixel-wise masks on the image data.

In some implementations, generating the machine learning model includes receiving image data including ground truth scores; labeling the image data; performing frame sampling and score assignment to the frames; applying training data to the machine learning model at a frame level and at a case level; optimizing the machine learning model with validation data at the frame level and the case level; applying test data that is not annotated; and performing case level evaluation of the test data.

In some implementations, the process 600 includes applying a second machine learning model that is different from the machine learning model, to patient data representing a treatment outcome for a treatment between the first time period and the second time period; generating, by the second machine learning model based on applying the second machine learning model to the patient data, a second prediction of disease progression of IBD in the patient; generating, based on the prediction and the second prediction, a recommendation for a treatment for IBD for the patient for a future time period.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

What is claimed is:

1. A method for predicting inflammatory bowel disease (IBD) activity in a patient and prescribing treatment for IBD, the method comprising:
   obtaining image data including endoscopic images of a gastrointestinal tract (GI) of a patient for a first time period and a second time period;
   determining one or more features to extract from the image data, the features each representing a physical parameter of the GI tract for each of the first time period and the second time period;
   extracting the one or more features from the image data to form a first feature vector for the first time period and a second feature vector for the second time period;
   selecting a machine learning model based on the one or more features included in the first feature vector and the second feature vector;
   processing the first feature vector and the second feature vector using the machine learning model, the machine learning model being trained with labeled image data representing instances of symptoms of IBD being in the GI tract, the labeled image data associating scores representing a progression of IBD based on the respective instances of the symptoms in the first and second vectors;
   determining, based on the processing, a prediction of disease progression of IBD in the patient; and
   storing, in a data store, the prediction in association with the image data.

2. The method of claim 1, wherein determining the prediction comprises:
   determining one or more frame level annotations corresponding to individual frames of a video of the image data;
   determining one or more case level annotations for the video of the image data; and
   determining, based on the one or more frame level annotations and the one or more case level annotations, the prediction of disease progression of IBD in the patient.

3. The method of claim 1, wherein the one or more features comprise values representing at least one of:
   a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal;
   wherein the machine learning model generates a score representing a severity of IBD at the respective first time period or second time period; and
   wherein the prediction of disease progression of IBD in the patient is based on the score representing a severity of IBD at the respective first time period or second time period.

4. The method of claim 1, further comprising:
   receiving electronic medical records (EMR) data for the patient, the EMR data including medical information about the patient, wherein the machine learning model is trained with labeled EMR data associating values of medical information of patients with respective severity of IBD in the patients;
   extracting one or more values from the EMR data to form an EMR feature vector;
   processing, by the machine learning model or by a second machine learning model in addition to the machine learning model, the EMR feature vector; and
   generating an updated prediction of disease progression of IBD in the patient indicated by the EMR data.

5. The method of claim 4, wherein the one or more features of the EMR feature vector comprise values representing at least one of:
   an age of the patient, a sex of the patient, a reproductive history of the patient, a smoking status of the patient, a race or ethnicity of the patient, a presence or absence of an anal fissure in the patient, a fistula or abscess in the patient, and the presence or absence of one or more complications such as uveitis, pyoderma gangernosum, erythema nodosum, and/or arthralgia in the patient, serological profiling results of the patient, a history of medications prescribed to the patient, a history of surgery for the patient, a degree of induration for the patient, a presence or size of an abdominal mass in the patient, a history of flaring in the patient, a hospitalization history for the patient, and a history of thrombosis for the patient.

6. The method of claim 1, further comprising:
   receiving registry data for the patient, the registry data including patient data across patient populations, wherein the machine learning model is trained with labeled registry data associating values of for patient populations with respective severity of IBD in particular patients of the patient populations;
   extracting one or more values from the registry data to form a registry feature vector;
   processing, by the machine learning model or by a second machine learning model in addition to the machine learning model, the registry feature vector; and generating an updated prediction of disease progression of IBD in the patient indicated by the registry data.

7. The method of claim 6, wherein the one or more features of the registry feature vector comprise values representing at least one of:
results and other data from studies, experiments, and clinical trials that test treatment regimens that are associated with the patient including one or more of drug therapy, physical therapy, or surgery, specific diagnoses associated with the patient, procedures, and application of drugs associated with the patient.

8. The method of claim 1, further comprising:
receiving omics data for the patient, the omics data including genetic or molecular profiles of patient populations, wherein the machine learning model is trained with labeled omics data associating values of genetic or molecular profiles with respective severity of IBD in the patients of the patient populations;
extracting one or more values from the omics data to form an omics feature vector;
processing, by the machine learning model or by a second machine learning model in addition to the machine learning model, the omics feature vector; and
generating an updated prediction of disease progression of IBD in the patient indicated by the omics data.

9. The method of claim 8, wherein the one or more features of the omics feature vector comprise values representing at least one of:
transcriptomics data such as sets of RNA molecules, including mRNA, rRNA, tRNA, and other non-coding RNAs relevant to treatment outcomes; one or more phenotypic traits of the patient; microbiome data for the patient; genome sequencing for the patient; bisulfate sequencing (RRBS) data of the patient; ChIP-sequencing for the patient; HLA-DR genotyping for the patient; a 16s microbiome sequence from stool of the patient; a 16s microbiome sequence from a biopsy of the patient; epithelial cell profiling from biopsy of the patient; a single cell assay from a biopsy of the patient; a single-cell RNA sequence from a biopsy of the patient; fecal calprotectin or lactoferrin of the patient; Haematocrit levels for the patient; serum CRP/C-reactive protein levels in the patient; Pharmacokinetics (PK) data associated with a patient; white blood cell counts (WBC), hemoglobin (HgB), platelets, albumin, creatinine, and/or ESR levels of the patient; a urea analysis of the patient; liver function tests of the patient; ferritin, B12, Folate and/or VitD levels in the patient; SCFA levels in stool of the patient; and basal metabolite panel in the patient.

10. The method of claim 9, wherein the machine learning model comprises a convolutional neural network (CNN) or other models, and wherein the each of the instances of symptoms of IBD contributes to an activation value for inputting into a layer of the CNN.

11. The method of claim 1, wherein processing the feature vector comprises performing a classification with detection bounding boxes and segmentation pixel-wise masks on the image data.

12. The method of claim 1, further comprising generating the machine learning model by:
receiving image data including ground truth scores;
labeling the image data;
performing frame sampling and score assignment to the frames;
applying training data to the machine learning model at a frame level and at a case level;
optimizing the machine learning model with validation data at the frame level and the case level;
applying test data that is not annotated; and
performing case level evaluation of the test data.

13. The method of claim 1, further comprising applying a second machine learning model that is different from the machine learning model, to patient data representing a treatment outcome for a treatment between the first time period and the second time period;
generating, by the second machine learning model based on applying the second machine learning model to the patient data, a second prediction of disease progression of IBD in the patient; and
generating, based on the IBD severity score and the second prediction, a recommendation for a treatment for IBD for the patient for a future time period.

14. A system for predicting inflammatory bowel disease (IBD) activity in a patient and prescribing treatment for IBD, the system comprising:
at least one processor; and
at least one memory storing instructions that, when executing by the at least one processor, cause the at least one processor to perform operations comprising:
obtaining image data including endoscopic images of a gastrointestinal tract (GI) of a patient for a first time period and a second time period;
determining one or more features to extract from the image data, the features each representing a physical parameter of the GI tract for each of the first time period and the second time period;
extracting the one or more features from the image data to form a first feature vector for the first time period and a second feature vector for the second time period;
selecting a machine learning model based on the one or more features included in the first feature vector and the second feature vector;
processing the first feature vector and the second feature vector using the machine learning model, the machine learning model being trained with labeled image data representing instances of symptoms of IBD being in the GI tract, the labeled image data associating scores representing a progression of IBD based on the respective instances of the symptoms in the first and second vectors;
determining, based on the processing, a prediction of disease progression of IBD in the patient; and
storing, in a data store, the prediction in association with the image data.

15. The system of claim 14, wherein determining the prediction comprises:
determining one or more frame level annotations corresponding to individual frames of a video of the image data;
determining one or more case level annotations for the video of the image data; and
determining, based on the one or more frame level annotations and the one or more case level annotations, the prediction of disease progression of IBD in the patient.

16. The system of claim 14, wherein the one or more features comprise values representing at least one of:
a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal; and wherein the prediction of disease progression of IBD in the patient is based on the values of the one or more features.

17. The system of claim 14, further comprising:

receiving electronic medical records (EMR) data for the patient, the EMR data including medical information about the patient, wherein the machine learning model is trained with labeled EMR data associating values of medical information of patients with respective severity of IBD in the patients;

extracting one or more values from the EMR data to form an EMR feature vector;

processing, by the machine learning model or by a second machine learning model in addition to the machine learning model, the EMR feature vector; and generating an updated prediction of disease progression of IBD in the patient indicated by the EMR data.

18. The system of claim 14, further comprising applying a second machine learning model that is different from the machine learning model, to patient data representing a treatment outcome for a treatment between the first time period and the second time period;

generating, by the second machine learning model based on applying the second machine learning model to the patient data, a second prediction of disease progression of IBD in the patient; and generating, based on the the IBD severity score and prediction and the second prediction, a recommendation for a treatment for IBD for the patient for a future time period.

19. One or more non-transitory computer readable media storing instructions predicting inflammatory bowel disease (IBD) activity in a patient and prescribing treatment for IBD, the instructions configured to cause at least one processor executing the instructions to perform operations comprising:

obtaining image data including endoscopic images of a gastrointestinal tract (GI) of a patient for a first time period and a second time period;

determining one or more features to extract from the image data, the features each representing a physical parameter of the GI tract for each of the first time period and the second time period;

extracting the one or more features from the image data to form a first feature vector for the first time period and a second feature vector for the second time period;

selecting a machine learning model based on the one or more features included in the first feature vector and the second feature vector;

processing the first feature vector and the second feature vector using the machine learning model, the machine learning model being trained with labeled image data representing instances of symptoms of IBD being in the GI tract, the labeled image data associating scores representing a progression of IBD based on the respective instances of the symptoms in the first and second vectors;

determining, based on the processing, a prediction of disease progression of IBD in the patient; and storing, in a data store, the prediction in association with the image data.

20. The one or more non-transitory computer readable media of claim 19, further comprising applying a second machine learning model that is different from the machine learning model, to patient data representing a treatment outcome for a treatment between the first time period and the second time period;

generating, by the second machine learning model based on applying the second machine learning model to the patient data, a second prediction of disease progression of IBD in the patient; and generating, based on the IBD severity score and prediction and the second prediction, a recommendation for a treatment for IBD for the patient for a future time period.

* * * * *

UNITED STATES PATENT AND TRADEMARK OFFICE
CERTIFICATE OF CORRECTION

PATENT NO. : 12,046,368 B2
APPLICATION NO. : 17/383205
DATED : July 23, 2024
INVENTOR(S) : Jonathan Ng, Jean-Pierre Schott and Daniel Wang Page 1 of 1

It is certified that error appears in the above-identified patent and that said Letters Patent is hereby corrected as shown below:

In the Claims

<u>Claim 5</u>
Column 34, Line 47, delete "gangernosum," and insert --gangrenosum,--.

<u>Claim 18</u>
Column 37, Line 33, delete "the the" and insert --the--.
Column 37, Lines 33-34, delete "IBD severity score and prediction and the second prediction," and insert --IBD severity score and the second prediction,--.

<u>Claim 20</u>
Column 38, Lines 37-38, delete "IBD severity score and prediction and the second prediction," and insert --IBD severity score and the second prediction,--.

Signed and Sealed this
Tenth Day of September, 2024

Katherine Kelly Vidal
*Director of the United States Patent and Trademark Office*